US012059215B2

(12) United States Patent
Zhang et al.

(10) Patent No.: US 12,059,215 B2
(45) Date of Patent: Aug. 13, 2024

(54) NAVIGATION SYSTEM AND METHOD FOR JOINT REPLACEMENT SURGERY

(71) Applicants: BEIJING LONGWOOD VALLEY MEDICAL TECHNOLOGY CO. LTD, Beijing (CN); Yiling Zhang, Beijing (CN)

(72) Inventors: Yiling Zhang, Beijing (CN); Xingyu Liu, Beijing (CN)

(73) Assignee: BEI JING LONGWOOD VALLEY MEDICAL TECHNOLOGY CO. LTD (CN)

( * ) Notice: Subject to any disclaimer, the term of this patent is extended or adjusted under 35 U.S.C. 154(b) by 0 days.

(21) Appl. No.: 18/258,147

(22) PCT Filed: Jan. 22, 2021

(86) PCT No.: PCT/CN2021/073211
§ 371 (c)(1),
(2) Date: Jun. 16, 2023

(87) PCT Pub. No.: WO2022/126828
PCT Pub. Date: Jun. 23, 2022

(65) Prior Publication Data
US 2024/0065770 A1 Feb. 29, 2024

(30) Foreign Application Priority Data
Dec. 18, 2020 (CN) .......................... 202011511175.0

(51) Int. Cl.
| A61B 5/00 | (2006.01) |
| A61B 34/10 | (2016.01) |
| A61B 34/20 | (2016.01) |

(52) U.S. Cl.
CPC .............. *A61B 34/20* (2016.02); *A61B 34/10* (2016.02); *A61B 2034/105* (2016.02); *A61B 2034/2055* (2016.02); *A61B 2034/2068* (2016.02)

(58) Field of Classification Search
CPC ... A61B 34/10; A61B 34/20; A61B 2034/105; A61B 2034/2055; A61B 2034/2068
See application file for complete search history.

(56) References Cited

U.S. PATENT DOCUMENTS

| 2005/0281465 A1 | 12/2005 | Marquart et al. |
| 2019/0201155 A1 | 7/2019 | Gupta et al. |

FOREIGN PATENT DOCUMENTS

| CN | 102647962 A | 8/2012 |
| CN | 104684502 A | 6/2015 |

(Continued)

OTHER PUBLICATIONS

First Office Action for corresponding Chinese application No. 202011511175.0; dated Jun. 18, 2021 (17 pages) Machine Translation.

(Continued)

*Primary Examiner* — Joel F Brutus
(74) *Attorney, Agent, or Firm* — Mendelsohn Dunleavy, P.C.

(57) ABSTRACT

A navigation system and method for joint replacement surgery, the system comprising: a pre-operative planning module (1), configured to perform segmentation and reconstruction on the basis of acquired hip joint medical image data to obtain a hip joint three-dimensional model, and perform pre-operative planning to determine the position, size, and angle of a prosthesis placement; and a navigation alignment module (2), configured to determine the spatial position of the pelvis and femur on the basis of a pelvis reference frame and a femoral reference frame, perform alignment on the hip joint three-dimensional model on the basis of the spatial position relationship between a surgical probe and the pelvis reference frame and femoral reference frame to obtain a hip joint physical model, and control a surgical instrument clamping the prosthesis to place the prosthesis in the hip joint on the basis of the hip joint physical model. By means of the pre-operative planning of information such as the surgical access and prosthesis placement, and tracking the surgical instrument during the surgery by means of a spatial positioning method, the accuracy (Continued)

of surgery is improved and navigation support is provided to the physician, making the surgery safer and more efficient.

6 Claims, 16 Drawing Sheets

(56) References Cited

FOREIGN PATENT DOCUMENTS

| | | | |
|---|---|---|---|
| CN | 109890281 | A | 6/2019 |
| CN | 109925055 | A | 6/2019 |
| CN | 110974426 | A | 4/2020 |
| CN | 111179350 | A | 5/2020 |
| CN | 111345895 | A | 6/2020 |
| CN | 111467036 | A | 7/2020 |
| CN | 111938813 | A | 11/2020 |
| WO | 2017204832 | A1 | 11/2017 |

OTHER PUBLICATIONS

International Search Report and Written Opinion for corresponding International application No. PCT/CN2021/073211; dated Sep. 21, 2021 (24 pages) Machine Translation.

Extended European Search Report for corresponding European application No. 21904775.0; dated Mar. 5, 2024 (9 pages).

NAVIGATION SYSTEM AND METHOD FOR JOINT REPLACEMENT SURGERY

CROSS-REFERENCE TO RELATED APPLICATION

The present application claims priority to Chinese application No. 2020115111750 filed on Dec. 18, 2020, entitled "Navigation System and Method for Joint Replacement Surgery", which is hereby incorporated by reference in its entirety.

FIELD

The present application relates to the field of medical technologies, and in particular, to a navigation system and method for joint replacement surgery.

BACKGROUND

In recent years, hip replacement has been widely performed both at home and abroad as an effective clinical surgery for treating severe hip joint pain, deformity, and dysfunction. Although the development of medical imaging technology (such as CT, MRI, etc., which may display a 3D structure of a complex part) enables a doctor to make more comprehensive and accurate assessments of the condition of the patient than before, features or images are unsuitable during the surgery. The doctor still relies mainly on two-dimensional X-ray images during the surgery, and performs local analysis and diagnosis based on clinical experience, which is far from adequate for precise positioning and quantitative analysis of a lesion area. A traditional three-dimensional (3D) model reconstructed based on CT image data before the surgery has a low registration accuracy with an anatomical structure of the patient during the surgery, poor real-time performance and longer surgical time, which seriously affects the motivation of the doctor to use the 3D model. In addition, a traditional joint replacement surgery mainly relies on the surgical experience of the doctor, and an artificial joint is placed and implanted by traditional surgical tools and instruments, which results in low repeatability, poor accuracy, high surgical risk, and postoperative complications.

SUMMARY

(a) Problems to be Solved

Due to the aforementioned problems with the existing method, the present application provides a navigation system and method for joint replacement surgery.

(b) Summary of the Invention

An embodiment of the present application provides a navigation system for joint replacement surgery, including:
- a preoperative planning module, configured to segment and reconstruct a hip joint based on obtained medical image data of the hip joint to obtain a three-dimensional (3D) model of the hip joint, and perform a preoperative planning to determine a placement position, size and angle of a prosthesis based on the 3D model of the hip joint;
- a navigation registration module, configured to determine spatial positions of a pelvis and a femur by using an optical locator, a pelvic reference rack and a femoral reference rack, register the 3D model of the hip joint based on spatial position relationships between a surgical probe and both the pelvic reference rack and the femoral reference rack to obtain a physical model of the hip joint, and match the physical model of the hip joint with a preoperative planed model; and
- a handheld control module, configured to place an acetabular prosthesis in the hip joint by using a handheld control module instrument based on based on a registration result between a preoperative plan and the physical model of the hip joint, monitor the position of the prosthesis in real-time during surgery, and manually adjust a rotation center, anteversion angle, abduction angle, and insertion depth of the acetabular prosthesis by using a handheld control device to accurately perform the preoperative plan during the surgery.

In an embodiment of the present application, the preoperative planning module includes: a data obtaining submodule, a 3D model reconstruction submodule, an acetabular side plan determination submodule, a femoral side plan determination submodule and a plan determination submodule.

In an embodiment, the data obtaining submodule is configured to obtain the medical image data of the hip joint;
- the 3D model reconstruction submodule is configured to segment and reconstruct the hip joint based on the obtained medical image data of the hip joint to obtain a 3D model of the hip joint;
- the acetabular side plan determination submodule is configured to determine the rotation center, diameter, anteversion angle and abduction angle of the acetabular based on the 3D model of the hip joint, and determine the size and position of the acetabular side implant prosthesis based on the rotation center, diameter, anteversion angle and abduction angle of the acetabular and the coverage rate of the acetabular shell;
- the femoral side plan determination submodule is configured to determine the rotation center of a femoral head, the shape and anatomical axis of a femoral medullary cavity and the collodiaphyseal angle of the femur based on the 3D model of the hip joint and determine the size and position of the femoral side implant prosthesis based on the rotation center of the femoral head, the shape and anatomical axis of the femoral medullary cavity, the collodiaphyseal angle of femur, a leg length discrepancy and a femoral combined offset;
- the plan determination submodule is configured to determine whether an acetabular side prosthesis implantation plan determined by the acetabular side plan determination submodule and a femoral side prosthesis implantation plan determined by the femoral side plan determination submodule are suitable: in case that the acetabular side prosthesis implantation plan determined by the acetabular side plan determination submodule and the femoral side prosthesis implantation plan determined by the femoral side plan determination submodule are unsuitable, trigger the acetabular side plan determination submodule and the femoral side plan determination submodule to re-determine the acetabular side prosthesis implantation plan and the femoral side prosthesis implantation plan; in case that the acetabular side prosthesis implantation plan determined by the acetabular side plan determination submodule and the femoral side prosthesis implantation plan determined by the femoral side plan determination submodule are suitable, determine the acetabular side prosthesis implantation plan determined by the acetabular side plan determination submodule and the femoral side prosthesis implantation plan determined by the femoral side plan determination submodule as the preoperative plan scheme.

In an embodiment of the present application, the navigation registration module includes: a probe examination submodule, a femur marking submodule, a femur registration submodule, a femur neck osteotomy submodule, a reaming and femoral stem placing submodule, a pelvis marking submodule and a pelvis registration submodule.

In an embodiment, the probe examination submodule is configured to perform accuracy verification on the surgical probe by using a probe calibration rack;

the femur marking submodule is configured to sample spatial positions of three or more points on a femoral anatomical structure by using the surgical probe;

the femur registration submodule is configured to register the femur in the 3D model of the hip joint based on spatial position relationships between three or more points sampled on the femoral anatomical structure by using the surgical probe and the femoral reference rack;

the femur neck osteotomy submodule is configured to determine a position of the femur neck osteotomy based on a registration result of the femur in the 3D model of the hip joint;

the reaming and femoral stem placing submodule is configured to ream the femur and place the femoral stem based on the position of the femur neck osteotomy;

the pelvic femur marking submodule is configured to sample spatial positions of three or more points on an acetabular side structure by using the surgical probe; and the pelvic registration submodule is configured to register the acetabular side in the 3D model of the hip joint based on spatial position relationships between three or more points on the acetabular side structure sampled by using the surgical probe and the pelvic reference rack.

In an embodiment of the present application, the handheld control module includes: an acetabulum rasping submodule, an acetabulum press-fitting submodule and a reduction result submodule, where the acetabulum rasping submodule is configured to rasp the acetabulum by using the handheld control device based on the registration result of the acetabular side in the 3D model of the hip joint;

the acetabulum press-fitting submodule is configured to control the surgical instrument holding the acetabular shell to place the acetabular shell in the acetabulum and complete the press-fitting operation by using the handheld control device based on the physical model of the hip joint after rasping the acetabulum, where the control the surgical instrument holding the acetabular shell to place the acetabular shell in the acetabulum and complete the press-fitting operation by using the handheld control device refers to: manually adjust a rotation center, anteversion angle, abduction angle, and insertion depth of the acetabular prosthesis by using a handheld control device to accurately perform the preoperative plan during the surgery;

the reduction result submodule is configured to determine a surgical reduction result based on alignment between the femoral stem and the femoral anatomical structure, the placement position, a size, and an angle of the acetabular shell in the acetabulum.

In an embodiment of the present application, the reduction result submodule is configured to:

sample spatial positions of three or more points on the acetabular shell by using a surgical probe, determine the placement position, the size, and the angle of the acetabular shell in the acetabulum and measure the alignment between the femoral stem and the femoral anatomical structure to determine the surgical reduction result.

In an embodiment of the present application, the navigation registration module further includes a postoperative examination submodule, where the postoperative examination submodule is configured to examine the motion range and limb length of the hip joint to evaluate a postoperative stability of the hip joint after the surgical reduction.

In an embodiment of the present application, the handheld control module further includes an autorotation navigating submodule, where the autorotation navigating submodule is connected to a rasping positioning submodule, and is configured to drive the rasping positioning submodule to achieve adjustment in different directions of 360° to adapt to optical tracking and recognition in different directions.

An embodiment of the present application further provides a navigation method for joint replacement surgery, including:

segmenting and reconstructing the hip joint based on obtained medical image data of the hip joint to obtain a three-dimensional (3D) model of the hip joint, and performing a preoperative planning to determine a placement position, size and angle of a prosthesis based on the 3D model of the hip joint;

determining spatial positions of a pelvis and a femur by using an optical locator, pelvic reference rack and femoral reference rack; registering the 3D model of the hip joint based on spatial position relationships between the surgical probe and both the pelvic reference rack and the femoral reference rack to obtain a physical model of the hip joint, and matching the physical model of the hip joint with a preoperative planed model; and placing an acetabular prosthesis in the hip joint by using a handheld control module instrument based on a registration result between a preoperative plan and the physical model of the hip joint, monitoring the position of the prosthesis in real-time during surgery, and manually adjusting a rotation center, anteversion angle, abduction angle, and insertion depth of the acetabular prosthesis by using a handheld control device to accurately perform the preoperative plan during the surgery.

An embodiment of the present application further provides an electronic device, including a memory, a processor, and a computer program stored in the memory and executable on the processor, where when executing the computer program, the processor performs the steps of the navigation method for joint replacement surgery described above.

An embodiment of the present application further provides a non-transitory computer readable storage medium having a computer program stored thereon, where when executed by a processor, the computer program performs the steps of the navigation method for joint replacement surgery described above.

(c) Effects

In the navigation system and method for joint replacement surgery provided by embodiments of the present application, a 3D model of the hip joint is obtained before the surgery based on the medical image data of the hip joint, and then a preoperative plan is performed to stimulate a placement position, size and angle of a prosthesis and other information based on the 3D model of the hip joint. During the surgery, spatial positions of a femur and a pelvis are tracked by using a pelvic reference rack and a femoral reference rack, and the 3D model of the hip joint is registered based on spatial position relationships between a surgical probe, both the pelvic reference rack and the femoral reference rack. The structure of the hip joint of a patient may be accurately reflected through the 3D model of the hip joint, which allows a surgeon to have a very clear construe of the placement position of the prosthesis, and avoids complex processes of preoperative positioning and matching plan required by previous navigation systems. In embodiments of the present application, the preoperative plan is performed based on the 3D model, and intraoperative navigation is performed by using spatial positioning methods, which provides a doctor with visual surgical surgery monitoring information, assists the doctor in completing precise surgical operations, avoids dangerous areas to the maximum extent, and improves safety of the surgery.

BRIEF DESCRIPTION OF THE DRAWINGS

In order to more clearly illustrate the solutions disclosed in the embodiments of the present disclosure or the related art, the drawings used in the descriptions of the embodiments or the related art will be briefly described below. The drawings in the following description are only certain embodiments of the present disclosure, and other drawings may be obtained according to these drawings without any creative work for those skilled in the art.

DETAILED DESCRIPTION

The solutions in the embodiments of the present application are clearly and completely described in the following with reference to the accompanying drawings in the embodiments of the present application. These embodiments are only a part of the embodiments of the present application, and not all of the embodiments.

Figure 1:
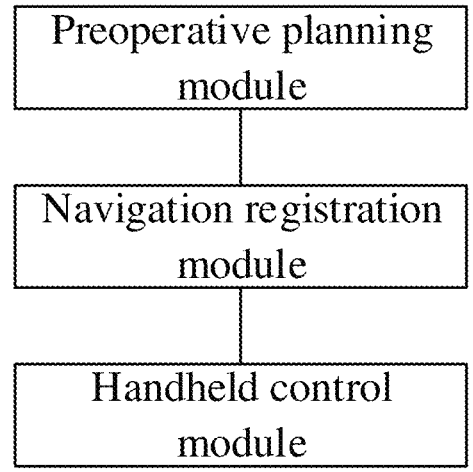
FIG. 1 is a schematic diagram of the structure of a navigation system for joint replacement surgery according to an embodiment of the present application.
Figure 4:
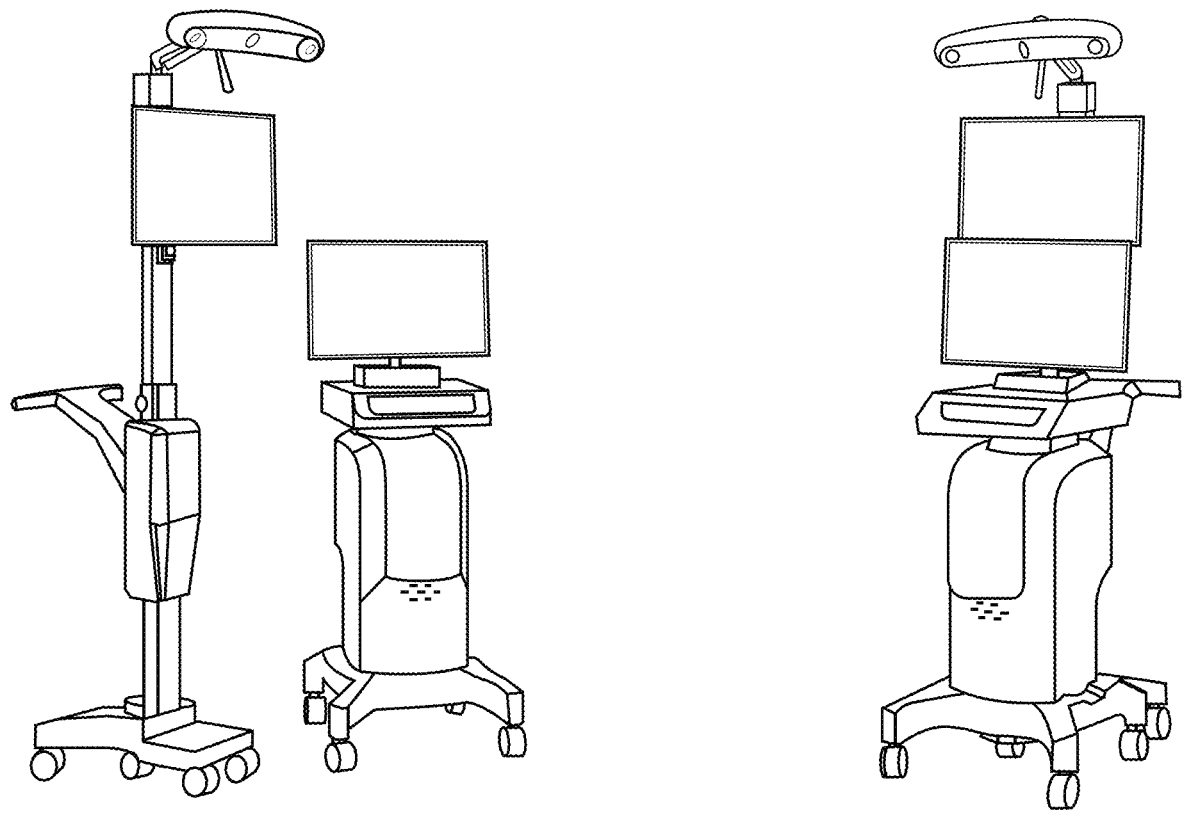
FIG. 4 is a schematic diagram of a navigation system for joint replacement surgery according to an embodiment of the present application.
Figure 5:
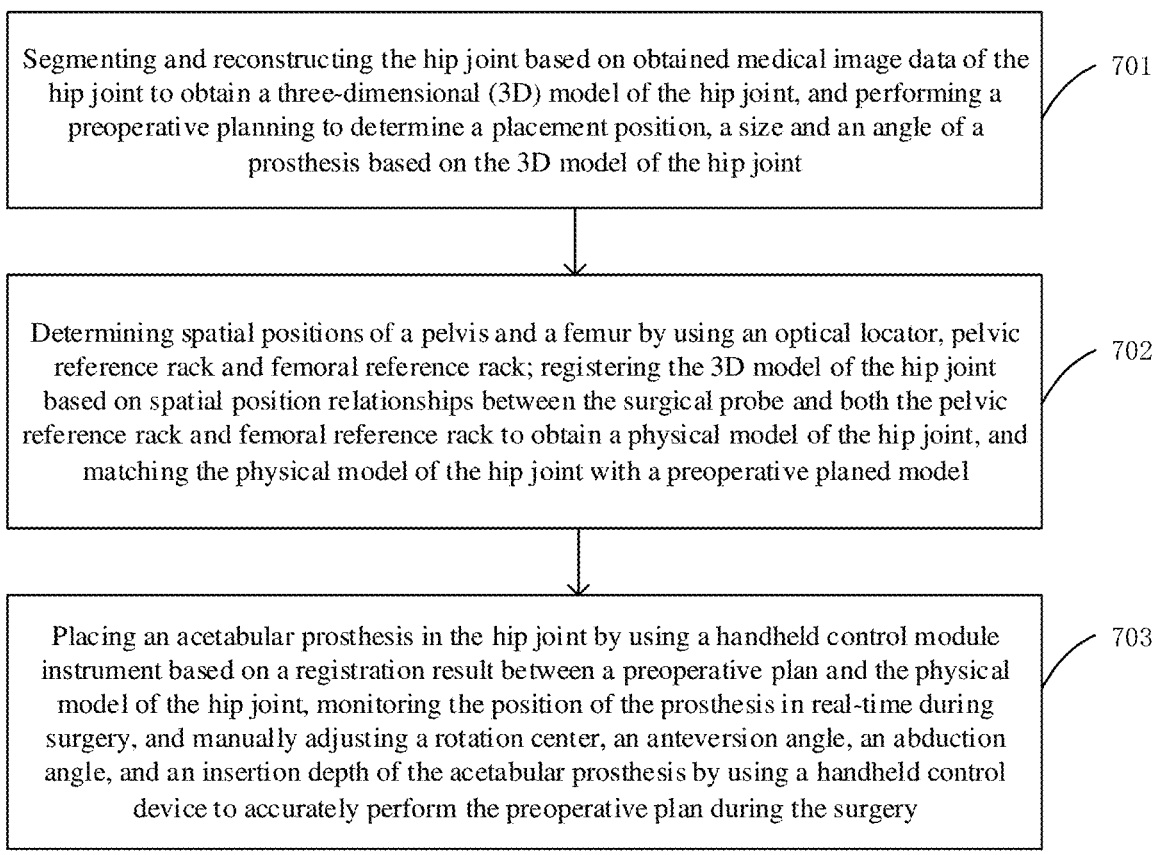
FIG. 5 is a flowchart of a navigation method for joint replacement surgery according to an embodiment of the present application.
Figure 6:
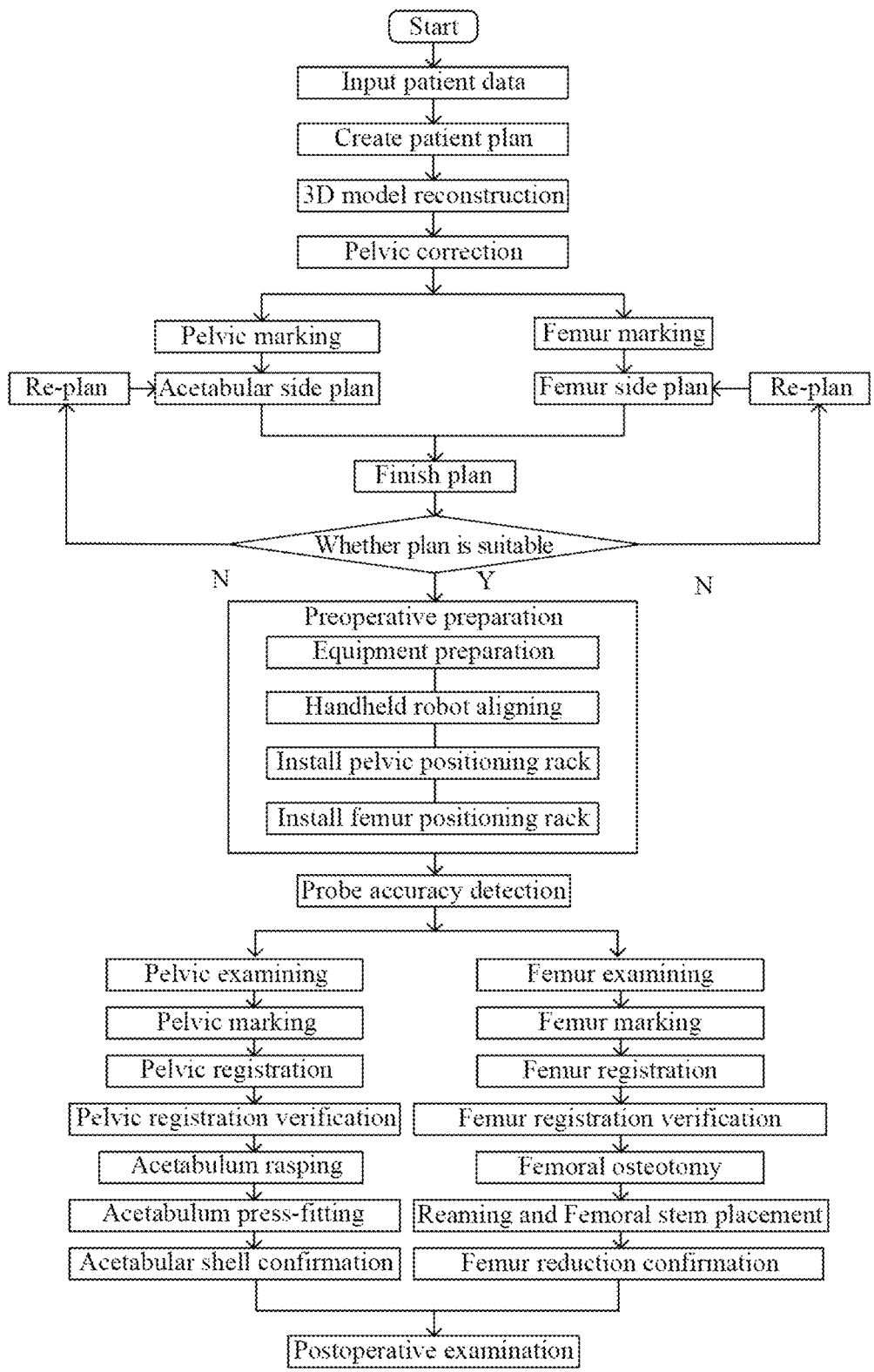
FIG. 6 is a flowchart of another navigation method for joint replacement surgery according to an embodiment of the present application.

FIG. 1 shows a navigation system for joint replacement surgery according to an embodiment of the present application. FIG. 4 is a schematic diagram of a navigation system for joint replacement surgery according to an embodiment of the present application. FIG. 5 is a flowchart of a navigation system for joint replacement surgery according to an embodiment of the present application; and FIG. 6 is a flowchart of another navigation system for joint replacement surgery according to an embodiment of the present application. Detailed explanation and description of the navigation system for joint replacement surgery according to embodiments of the present application will be provided in accompany with FIG. 1, FIG. 4, FIG. 5, and FIG. 6.

As shown in FIG. 1, an embodiment of the present application provides a navigation system for joint replacement surgery, including:

- a preoperative planning module, configured to segment and reconstruct a hip joint based on obtained medical image data of the hip joint to obtain a three-dimensional (3D) model of the hip joint, and perform a preoperative planning to determine a placement position, size and angle of a prosthesis based on the 3D model of the hip joint;
- a navigation registration module, configured to determine spatial positions of a pelvis and a femur by using an optical locator, a pelvic reference rack, and a femoral reference rack, register the 3D model of the hip joint to obtain a hip joint model based on spatial position relationships between a surgical probe and both the pelvic reference rack and the femoral reference rack, and match the physical model of the hip joint with a preoperative planed model; and
- a handheld control module, configured to place an acetabular prosthesis in the hip joint by using a handheld control module instrument based on a registration result between a preoperative plan and the physical model of the hip joint, monitor the position of the prosthesis in real-time during surgery, and manually adjust a rotation center, anteversion angle, abduction angle, and insertion depth of the acetabular prosthesis by using a handheld control device to accurately perform the preoperative plan during the surgery.

In an embodiment, preoperative scanning of the pelvis and both lower extremities of a patient may be performed by an imaging device (CT/MRI/X-ray) to generate a preoperative 3D view of the pelvis and both lower extremities. The navigation system for joint replacement surgery reads a CT image in DICOM format before the surgery, and segments the hip joint images to obtain a plurality of segmented images. A personalized complex hip joint 3D model including a virtual pelvis and a virtual femur may be reconstructed based on the image data corresponding to a plurality of segmented images (this step may be implemented by a traditional algorithm) to enable a surgeon to fully evaluate the condition of the patient before the surgery by using the hip joint 3D model and use a system software to plan a surgical approach and simulate a hip joint (the femoral side and acetabular side) surgical plan. The surgical plan includes surgical information such as the position, a size, and an angle of the implant of the prosthesis. Embodiments of the present application may achieve medical image processing on a regular computer, and allow a doctor to dissect visualized 3D images at will. In the navigation system for joint replacement surgery, lesion information is visually clear and easy for surgery operations.

Figure 16:
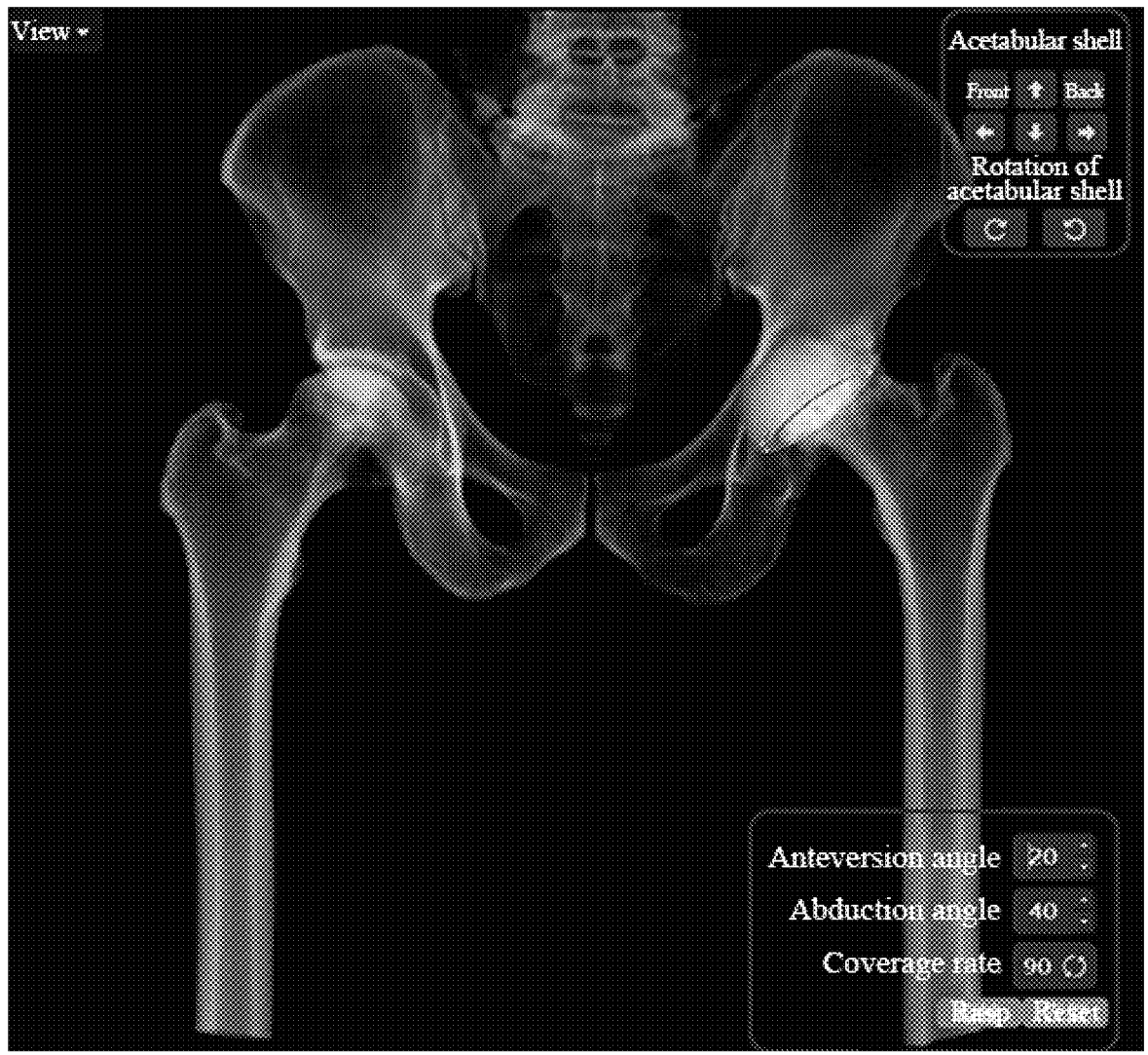
FIG. 16 is a schematic diagram of an acetabular shell plan of a navigation system for joint replacement surgery according to an embodiment of the present application.
Figure 17:
FIG. 17 is a schematic diagram of a femoral stem plan of a navigation system for joint replacement surgery according to an embodiment of the present application.
Figure 18:
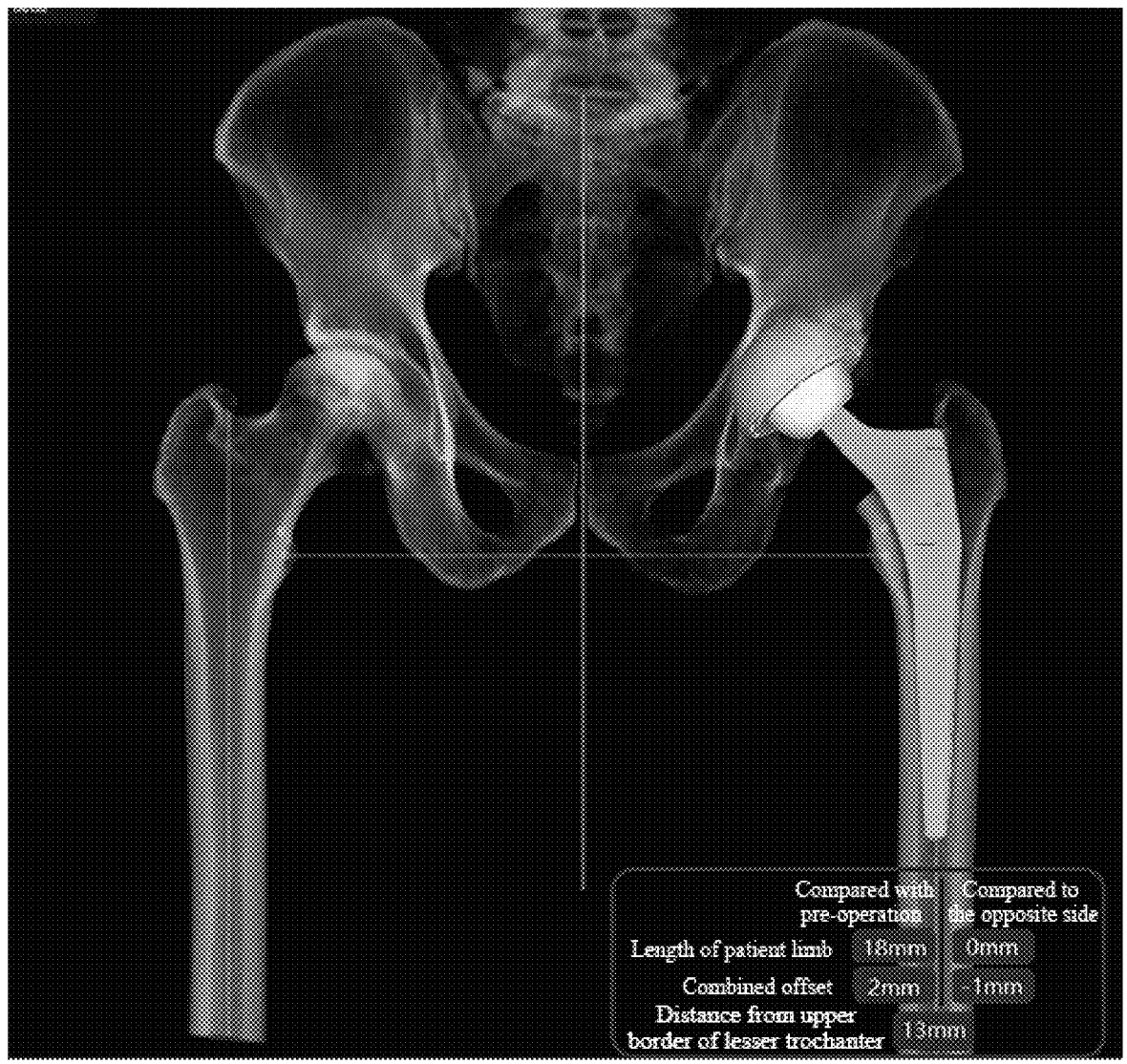
FIG. 18 is a schematic diagram of an osteotomy operation of a navigation system for joint replacement surgery according to an embodiment of the present application.

In an embodiment, as shown in FIG. 16, FIG. 17, and FIG. 18, the navigation system for joint replacement surgery is imported through a computer system, including measurement of acetabular shape, acetabular rotation center, bone mass, acetabular abduction angle and anteversion angle, leg length discrepancy and offset. During the surgery, all data may be templated based on actual measurement data and displayed on the computer timely to determine the most suitable size and position of the prosthesis.

In an embodiment, the handheld control module is also referred as a handheld robot or a handheld robot module.

In an embodiment, the pelvic reference rack and the femoral reference rack may be manually placed on the acetabular side and the femoral side, and a tracing element on the pelvic reference rack and femoral reference rack may be tracked by using a navigation camera of the system to determine spatial positions of the pelvis and femur of the patient. Correspondingly, the navigation camera tracks a tracing element at the tail of the surgical probe during the sampling of surgical probe points. Spatial positions of the sampled points are calculated through an algorithm, and thus spatial positions of the surgical probe, the pelvic reference frame and the femoral reference frame are integrated into a common coordinate system to register the 3D model of the hip joint. Corresponding sampled points will be displayed in the 3D model of the hip joint, and precise registration of surfaces of femoral side and acetabular side will be performed through a point cloud registration algorithm. It may be understood that the navigation registration module needs to perform a coordinate system registration between the intraoperative position of the patient and preoperative scanning data (such as CT and MRI) to find a conversion relationship between the preoperative scanning data and the intraoperative position of the patient, and modify the 3D model of the hip joint generated by the preoperative plan based on the intraoperative position of the patient to reduce the error in spatial positions of marked points during the preoperative plan process, thereby improving the registration accuracy greatly.

In an embodiment of the present application, a point cloud selected in the scanning data before the surgery is fitted with a point cloud calibrated by the doctor to find the most suitable rotation matrix. When calibrating a point on the body of the patient, the doctor will refer to the point selected before the surgery. In case that the point calibrated by the doctor and the point selected before the surgery are not in the same position on the body, the position of the selected point cloud before the surgery needs to be corrected in real-time based on the spatial position relationship and structure of the point cloud calibrated by the doctor, so as to make a final registration result have relatively high accuracy.

In an embodiment, after registration is completed between the femoral side and the acetabular side, the acetabular side is rasped and the femur is reamed. A predetermined type of acetabular shell and femoral stem are implanted into the femoral side and the acetabular side respectively after rasping the acetabular side and reaming the femur. The navigation camera dynamically tracks a current position of the surgical instrument relative to an anatomical structure of the patient through infrared imaging. Hip replacement surgery requires high surgical requirements, but traditional instrument assistance easily leads to uncertainty of the placement of the prosthesis, which takes a considerable amount of time to implant the prosthesis into a correct position. In embodiments of the present application, advanced imaging devices (CT/MRI/X-ray) are integrated, 3D models of the pelvis and both lower extremities are obtained based on an imaging examination result, and computer-aided medical imaging technology is used for 3D image reconstruction and fusion. The condition of the patient is fully evaluated before the surgery, a surgical path is planned to simulate a surgical plan, and a surgical approach and surgical information such as the size, position, and angle of prosthesis placement are determined. By tracking the surgical instrument through the spatial positioning method, the accuracy and feasibility of the surgery are significantly improved and navigation supports are provided for surgeons, which makes the surgery more accurate, safe, and efficient.

Figure 2:
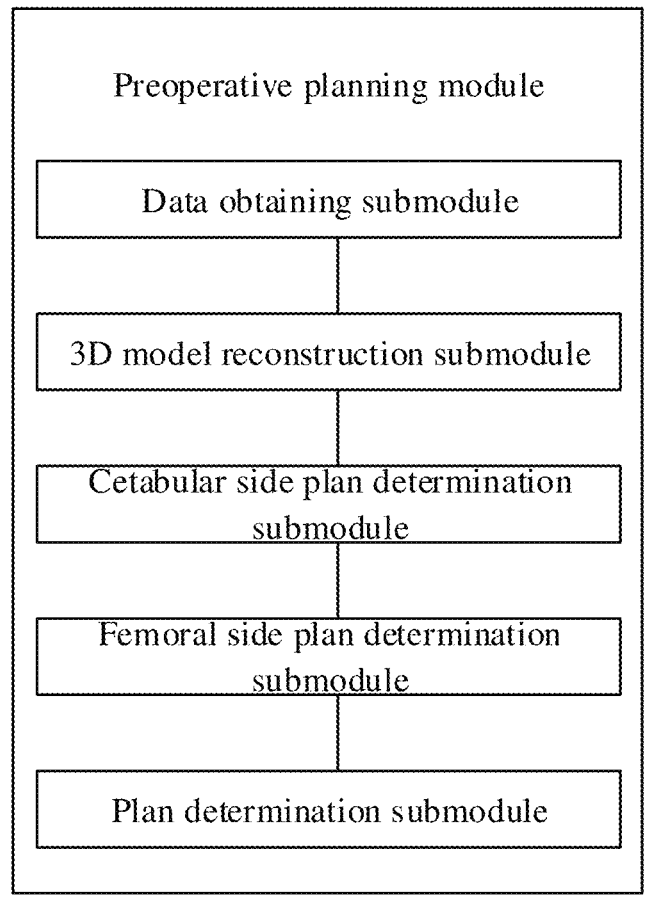
FIG. 2 is a schematic diagram of a preoperative planning module of a navigation system for joint replacement surgery according to an embodiment of the present application.

Based on the above-mentioned embodiments, as shown in FIG. 2, the preoperative planning module includes: a data obtaining submodule, a 3D model reconstruction submodule, an acetabular side plan determination submodule, a femoral side plan determination submodule, and a plan determination submodule, where the data obtaining submodule is configured to obtain the medical image data of the hip joint;

the 3D model reconstruction submodule is configured to segment and reconstruct the hip joint based on the obtained medical image data of the hip joint to obtain a 3D model of the hip joint;

the acetabular side plan determination submodule is configured to determine the rotation center, diameter, anteversion angle and abduction angle of the acetabular based on the 3D model of the hip joint, and determine the size and position of the acetabular side implant prosthesis based on the rotation center, diameter, anteversion angle and abduction angle of the acetabular and the coverage rate of the acetabular shell.

For example, when the acetabular diameter of the 3D model of the hip joint is 50 mm, the corresponding size of the acetabular side implant prosthesis is determined to be about 50 mm. The specific position of the acetabular implant prosthesis is determined based on the position of the acetabular rotation center and ensuring that the coverage rate of the acetabular shell is greater than 70% when the acetabular anteversion angle is 200 and the acetabular abduction angle is 40°.

The femoral side plan determination submodule is configured to determine the rotation center of a femoral head, the shape and anatomical axis of a femoral medullary cavity and the collodiaphyseal angle of the femur based on the 3D model of the hip joint and determine the size and position of the femoral side implant prosthesis based on the rotation center of the femoral head, the shape and anatomical axis of the femoral medullary cavity, the collodiaphyseal angle of femur, a leg length discrepancy and a femoral combined offset.

In an embodiment, the rotation center of the femoral head may be determined based on the femoral head rotation center, and the femoral prosthesis axis may be determined based on the anatomical axis of the femoral medullary cavity. The size of the femoral prosthesis may be determined based on the shape of the femoral medullary cavity and the collodiaphyseal angle.

The plan determination submodule is configured to determine whether an acetabular side prosthesis implantation plan determined by the acetabular side plan determination submodule and a femoral side prosthesis implantation plan determined by the femoral side plan determination submodule are suitable: in case that the acetabular side prosthesis implantation plan determined by the acetabular side plan determination submodule and the femoral side prosthesis implantation plan determined by the femoral side plan determination submodule are unsuitable, trigger the acetabular side plan determination submodule and the femoral side plan determination submodule to re-determine the acetabular side prosthesis implantation plan and the femoral side prosthesis implantation plan; in case that the acetabular side prosthesis implantation plan determined by the acetabular side plan determination submodule and the femoral side prosthesis implantation plan determined by the femoral side plan determination submodule are suitable, determine the acetabular side prosthesis implantation plan determined by the acetabular side plan determination submodule and the femoral side prosthesis implantation plan determined by the femoral side plan determination submodule as the preoperative plan scheme.

In an embodiment, the determining whether an acetabular side prosthesis implantation plan determined by the acetabular side plan determination submodule and a femoral side prosthesis implantation plan determined by the femoral side plan determination submodule are suitable refers to:

a standard for the size of the acetabular side prosthesis being suitable: the diameter of the acetabular shell is approximately equal to the diameter of the acetabulum, the acetabular shell fits with the anterior and posterior diameters of the acetabulum but does not wear too much bone, the coverage rate of the acetabular shell is ensured to be greater than 70%; a standard for the position of the acetabular shell being suitable: the acetabular shell is placed in a safe area; a standard for the femur being suitable: the femoral side prosthesis adheres to the femur.

In an embodiment, the preoperative planning module includes three parts: a human-machine interaction interface, a motor control, and an image signal obtaining, which are all programmed in C++ and may run in the Windows operating system. Intraoperative surgical images and plan surgical paths can be transmitted, intraoperative navigation is performed by controlling the data network interface of this module. The system adopts an integrated design concept, which makes the system structure compact and occupies less surgical space. This modular design allows the system to be easily disassembled and assembled, which not only improves the clinical adaptability of the system but also facilitates disinfection. Moreover, the system has no special requirements for the surgical environment and surgical instruments.

In an embodiment, fast interface technology (data interface and mechanical interface) is used between functional modules to facilitate the assembly of the framework and the connection of drive motors and cables.

In the navigation system for joint replacement surgery provided by embodiments of the present application, a 3D model of the hip joint is obtained before the surgery based on the medical image data of the hip joint, and then a preoperative plan is performed to stimulate a placement position, size and angle of a prosthesis and other information based on the 3D model of the hip joint. During the surgery, spatial positions of a femur and a pelvis are tracked by using a pelvic reference rack and a femoral reference rack, and the 3D model of the hip joint is registered based on spatial position relationships between a surgical probe and both the pelvic reference rack and the femoral reference rack. The structure of the hip joint of a patient may be accurately reflected through the 3D model of the hip joint, which allows a surgeon to have a very clear construe of the placement position of the prosthesis, and avoids complex processes of preoperative positioning and matching plan required by previous navigation systems. In embodiments of the present application, the preoperative plan is performed based on the 3D model, and intraoperative navigation is performed by using spatial positioning methods, which provides a doctor with visual surgical surgery monitoring information, assists the doctor in completing precise surgical operations, avoids dangerous areas to the maximum extent, and improves safety of the surgery.

In an embodiment, the navigation system for joint replacement surgery segments the hip joint image into a plurality of segmented images after reading DICOM format CT images before the surgery, to obtain image data corresponding to the plurality of segmented images.

In an embodiment, a personalized complex hip joint 3D model including the virtual pelvis and femur is reconstructed based on the image data obtained from the data obtaining submodule.

In an embodiment, the surgeon may develop a plan for rasping acetabular and implanting acetabular shell based on the structure of the acetabular side in the 3D model of the hip joint, including information such as surgical approached, rasping frequency, size, position, and angle of the acetabular shell.

In an embodiment, the surgeon may formulate the plan for implanting the femur neck osteotomy and the prosthesis based on the structure of the femoral side in the 3D model of the hip joint, including the position of the osteotomy, reaming degree, position, size and angle of the femoral stem and other information.

In an embodiment, after developing the acetabular side plan and femoral side plan, the surgeon needs to perform evaluation and analysis, and re-develop the surgical plan that do not meet the standard to ensure that the surgical plan generated by preoperative plan is the best plan. The embodiments of the present application may provide convenience for the doctor to perform surgical operations from visual, tactile, and auditory perspectives, expand operational skills of the doctor, effectively improve the quality of surgical diagnosis and evaluation, precision operations, and surgical training, and shorten the rehabilitation cycle of the patient.

In an embodiment, the preoperative plan process may further include: a plan creating submodule configured to create a plan for a patient, a pelvic correcting submodule configured to correct the 3D model of the pelvic, a pelvic marking submodule configured to mark the preoperative acetabular (acetabular front edge, acetabular rear edge, acetabular upper edge, acetabular rotation center), an acetabular registration planning submodule configured to perform preoperative acetabular registration, an acetabular verification planning submodule configured to perform preoperative acetabular verification, a femur marking submodule configured to perform preoperative femur marking (femoral tibial saddle point, lesser trochanter point, medial epicondyle of knee, lateral epicondyle of knee, greater trochanter point, femoral tibial center, femoral head center, proximal femur and distal femur), a femur registration planning submodule configured to perform preoperative femur registration, and a femur verification planning submodule configured to perform preoperative femur verification.

The acetabular registration planning submodule and the femoral registration planning submodule use points planned before the surgery to perform registration after intraoperative sampling. The acetabular verification planning submodule and femoral verification planning submodule are both configured to verify whether the registration of the acetabular side and femoral side is successful. Three or more points on the surface of the structure are sampled by using the surgical probe again for registration verification after registration on the acetabular side and femoral side.

Figure 3:
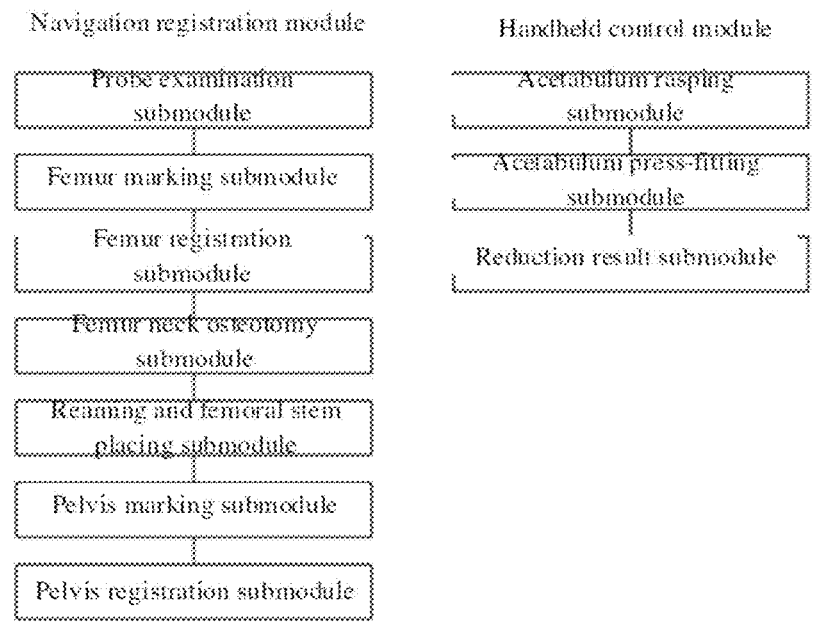
FIG. 3 is a schematic diagram of a navigation registration module of a navigation system for joint replacement surgery according to an embodiment of the present application.

Based on the above-mentioned embodiments, as shown in FIG. 3, a schematic diagram of a navigation registration module of a navigation system for joint replacement surgery is provided by an embodiment of the present application. The navigation registration module includes:

a probe examination submodule, a femur marking submodule, a femur registration submodule, a femur neck osteotomy submodule, a reaming and femoral stem placing submodule, a pelvis marking submodule and a pelvis registration submodule, where the probe examination submodule is configured to perform accuracy verification on the surgical probe by using a probe calibration rack;

the femur marking submodule is configured to sample spatial positions of three or more points on a femoral anatomical structure by using the surgical probe;

the femur registration submodule is configured to register the femur in the 3D model of the hip joint based on spatial position relationships between three or more points on the femoral anatomical structure sampled by using the surgical probe and the femoral reference rack;

the femur neck osteotomy submodule is configured to determine a position of the femur neck osteotomy based on a registration result of the femur in the 3D model of the hip joint;

the reaming and femoral stem placing submodule is configured to ream the femur and place the femoral stem based on the position of the femur neck osteotomy;

the pelvic femur marking submodule is configured to sample spatial positions of three or more points on an acetabular side structure by using the surgical probe; and the pelvic registration submodule is configured to register the acetabular side in the 3D model of the hip joint based on spatial position relationships between three or more points on the acetabular side structure sampled by using the surgical probe and the pelvic reference rack.

In an embodiment, when the femoral registration submodule or pelvic registration submodule is performing registration, the femoral registration submodule or pelvic registration submodule is configured to:

take a triangle as the smallest unit in the registration process, if the points marked by the doctor during the surgery are A, B and C, the corresponding preoperative plan points are a, b and c, where the points marked by the doctor are all on the surface of human tissue;

select corresponding points a', b' and c' from neighborhood spatial point sets corresponding to a, b, and c respectively to make the triangle ABC and triangle a'b'c' congruent, where all three points a', b' and c' are on the surface of human tissue, and the triangle consisted of a', b' and c' and the triangle consisted of A, B and C are congruent triangles; and correct spatial positions of a, b, and c planned before the surgery to the spatial positions of a', b', and c', and register the points marked during the surgery with the points planned before the surgery by using a registration mode, to achieve accurate registration on surfaces of the femoral side and the acetabular side.

Figure 12:
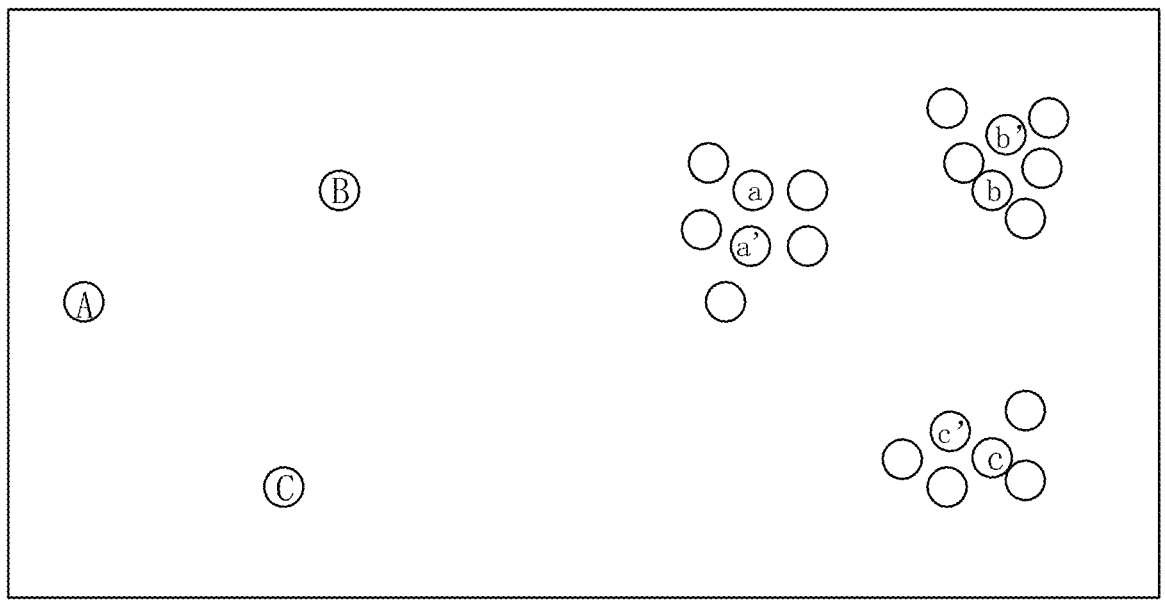
FIG. 12 is a schematic diagram of a registration process of a navigation system for joint replacement surgery according to an embodiment of the present application.

Using the surgical probe to sample points on three or more patient anatomical structures is taken as an example. The minimum unit of this registration algorithm is a triangle. Assuming that the points marked by the doctor during the surgery are A, B and C, and the corresponding preoperative plan points are a, b, and c, and it may be defaulted that the points marked by the doctor are all on the surface of human tissue. Therefore, points a', b' and c' need to be found in the neighborhood of a, b and c, to make the triangle ABC and triangle a'b'c' congruent, where points a'b'c' are all on the surface of human tissue, resulting in a high degree of overlap between the positions of points a'b'c' and points ABC on the human tissue, as the triangle has uniqueness. As shown in FIG. 12, a schematic diagram of the registration process of a navigation system for joint replacement surgery is provided by an embodiment of the present application. On the left side of this figure, A, B and C are the points marked by the doctor during the surgery, and a, b and c on the right side are the points planned before the surgery. It may be seen that (A, B, C) and (a, b, c) have a significant spatial position error, and blank marked points on the right side are point sets in the neighborhood space of a, b and c. a', b' and c' are selected from a large number of blank marked points. The triangle consisted of a', b' and c' and the triangle consisted of A, B and C are basically congruent triangles. At this time, Spatial positions of a, b, and c planned before the surgery are adjusted to spatial positions of a', b' and c', and an ICP registration mode is used to register the points marked during the surgery with the points planned before the surgery, so as to achieve accurate registration of the surfaces of the femoral side and the acetabular side.

It may be understood that due to its uniqueness and sufficient stability, the triangle is taken as the minimum registration unit during the registration, which can effectively improve the accuracy of registration, thus achieving accurate registration of the surfaces of the femoral side and the acetabular side.

Based on the above-mentioned embodiments, the handheld control module includes: an acetabulum rasping submodule, an acetabulum press-fitting submodule and a reduction result submodule, where the acetabulum rasping submodule is configured to rasp the acetabulum by using the handheld control device based on the registration result of the acetabular side in the 3D model of the hip joint;

the acetabulum press-fitting submodule is configured to control the surgical instrument holding the acetabular shell to place the acetabular shell in the acetabulum and complete the press-fitting operation by using the handheld control device based on the physical model of the hip joint after rasping the acetabulum, where the control the surgical instrument holding the acetabular shell to place the acetabular shell in the acetabulum and complete the press-fitting operation by using the handheld control device refers to: manually adjust a rotation center, anteversion angle, abduction angle, and insertion depth of the acetabular prosthesis by using a handheld control device to accurately perform the preoperative plan during the surgery;

the reduction result submodule is configured to determine a surgical reduction result based on alignment between the femoral stem and the femoral anatomical structure, the placement position, a size, and an angle of the acetabular shell in the acetabulum.

In an embodiment, accuracy verification for the surgical probe is required before intraoperative sampling. The tip of the surgical probe will be tapped to each examining point on the calibration rack of the probe in turn. After tapping all examining points, the sampling accuracy of the surgical probe will be displayed on the system. The surgical probe that does not meet the preset standards will be adjusted to meet the surgical operation requirements.

In an embodiment, the tip of the surgical probe is used to tapped three or more different positions on the acetabular side and the femoral side during the surgery, and the femur in the 3D model of the hip joint is registered based on spatial position relationships between three or more points on the femoral anatomical structure sampled by using the surgical probe and the femoral reference rack. The acetabular side in the 3D model of the hip joint is registered based on spatial position relationships between three or more points on the acetabular side structure sampled by the surgical probe and the pelvic reference rack.

Figure 19:
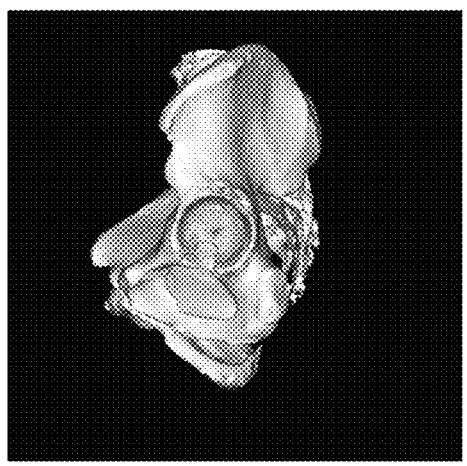
FIG. 19 is a schematic diagram of a rasping operation of a navigation system for joint replacement surgery according to an embodiment of the present application.
Figure 20:
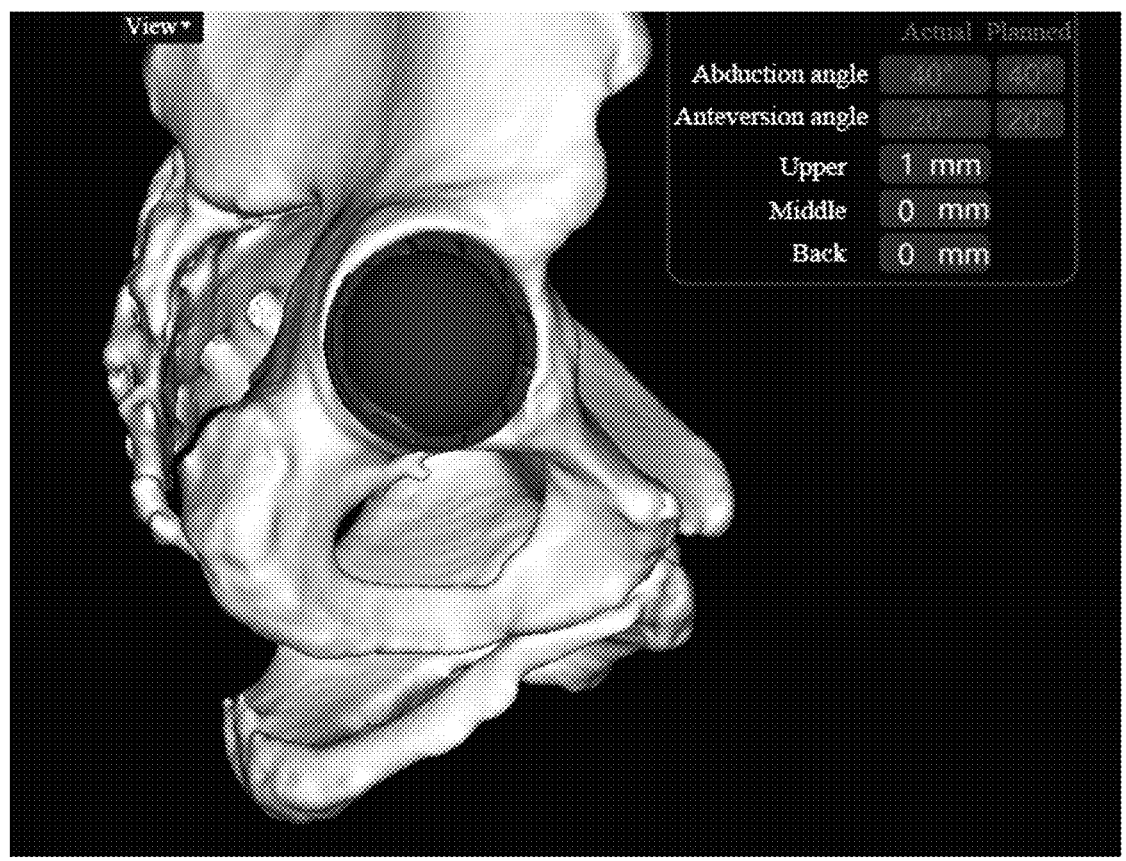
FIG. 20 is a schematic diagram of a press-fitting operation of a navigation system for joint replacement surgery according to an embodiment of the present application.

As shown in FIG. 19 and FIG. 20, after registering the acetabular side in the 3D model of the hip joint, the acetabulum is rasped to control the surgical instrument clamping the acetabular shell to place the acetabular shell in the acetabulum, and the press-fitting operation is completed.

Figure 21:
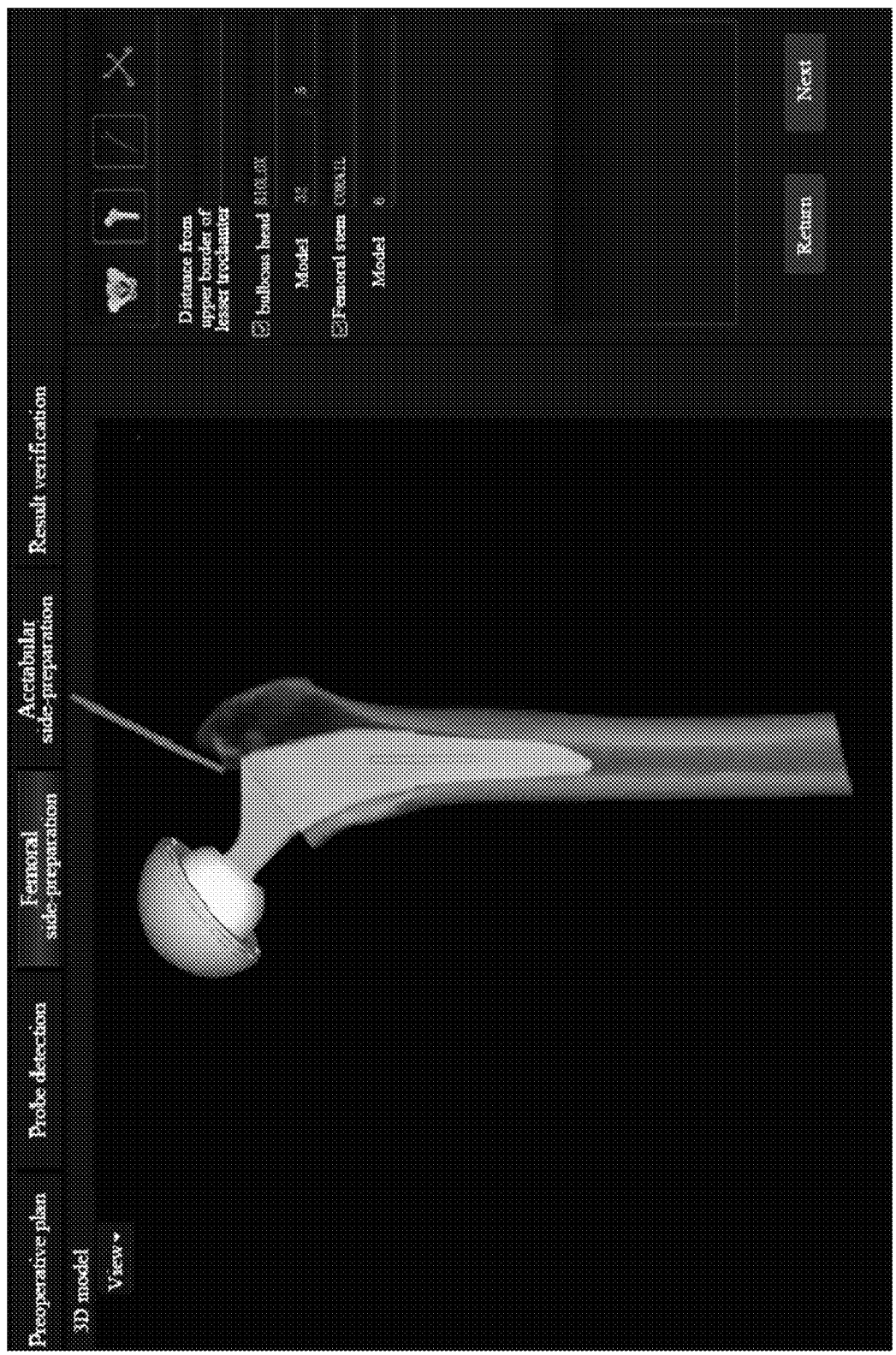
FIG. 21 is a schematic diagram of a reduction operation of a navigation system for joint replacement surgery according to an embodiment of the present application.

As shown in FIG. 21, after implanting the femoral stem and acetabular shell, whether to perform the surgical reduction is determined based on alignment between the femoral stem and the femoral anatomical structure, the placement position, the size, and the angle of the acetabular shell in the acetabulum.

In an embodiment, the navigation registration module may further include a pelvic registration verification submodule configured to verify pelvic registration results and a femoral registration verification submodule configured to verify femoral registration results. After completing the registration on the acetabular side and the femoral side, whether the registration is correct is verified based on the distance between the registered sampling point and the bone surface.

In an embodiment, a personalized pelvic model is established through optical tracking software and the position of the acetabular prosthesis is simulated by the tracking system. During the entire implantation process, the data of the angle of acetabular prosthesis are always displayed on a computer screen, and the position of the acetabular prosthesis is updated and displayed in real-time in the form of simulation, which makes the surgeon have a clear understanding about the position of the prosthesis, avoids the tedious process of preoperative positioning and matching plan required by a traditional navigation system. The system software may accurately detect and calculate the 3D data of an object, and determine specific orientations and angles of the object.

Based on the above-mentioned embodiments, the reduction result submodule is configured to:

sample spatial positions of three or more points on the acetabular shell by using a surgical probe, determine the placement position, the size, and the angle of the acetabular shell in the acetabulum and measure the alignment between the femoral stem and the femoral anatomical structure to determine the surgical reduction result.

In an embodiment, the tip of the surgical probe is used to tap the spatial positions of three or more points on the acetabular shell after the implantation of the acetabular shell. The acetabular side in the 3D model of the hip joint is registered based on spatial position relationships between the points sampled by the surgical probe and the pelvic reference rack, to determine the placement position, the size, and the angle of the acetabular shell in the acetabulum. For example, the anteversion angle of the acetabular shell, abduction angle of the acetabular shell, coverage rate of the acetabular shell, and relative position change between the acetabular shell rotation center and the original acetabular rotation center are determined to determine whether to perform the surgical reduction.

In an embodiment, after implanting of the femoral stem, the alignment between the femoral stem and the femoral anatomical structure is measured, such as leg length discrepancy, femoral offset difference, combined offset difference, femoral anteversion angle, etc., so as to determine whether to perform the surgical reduction.

Based on the above-mentioned embodiments, the navigation registration module further includes a postoperative examination submodule, where the postoperative examination submodule is configured to examine the motion range and limb length of the hip joint to evaluate a postoperative stability of the hip joint after the surgical reduction.

In an embodiment, after the surgical reduction, the postoperative stability of the hip joint is evaluated by checking the motion range of the hip joint and the length of both lower extremities, the articular capsule is sutured, and the tissue layers are closed layer by layer.

In an embodiment, after completing the entire hip replacement surgery, the variation of the acetabular prosthesis abduction angle is reduced. The prosthesis is more compatible with the human body, the prosthesis installation process is more accurate, the surgical quality is significantly improved, and some postoperative complications may be effectively avoided.

Another embodiment of the present application provides a navigation method for joint replacement surgery. Referring to FIG. 5, a flowchart of a navigation method for joint replacement surgery is provided by an embodiment of the present application. Referring to FIG. 6, a flowchart of another navigation method for joint replacement surgery is provided by an embodiment of the present application. As shown in FIG. 5 and FIG. 6, a navigation method for joint replacement surgery is provided by embodiment of the present application, which includes the following steps.

Step 701: segmenting and reconstructing the hip joint based on obtained medical image data of the hip joint to obtain a three-dimensional (3D) model of the hip joint, and performing a preoperative planning to determine a placement position, size and angle of a prosthesis based on the 3D model of the hip joint.

In step 701, preoperative scanning of the pelvis and both lower extremities of a patient may be performed by an imaging device (CT/MRI/X-ray) to generate a preoperative 3D view of the pelvis and both lower extremities. The navigation system for joint replacement surgery reads a CT image in DICOM format before the surgery, and segments the hip joint images to obtain a plurality of segmented images. A personalized complex hip joint 3D model including a virtual pelvis and a virtual femur may be reconstructed based on the image data corresponding to a plurality of segmented images to enable a surgeon to fully evaluate the condition of the patient before the surgery by using the hip joint 3D model and use a system software to plan a surgical approach and simulate a hip joint (the femoral side and acetabular side) surgical plan. The surgical plan includes surgical information such as the position, the size, and the angle of the implant of the prosthesis.

In this step, the navigation system for joint replacement surgery is imported through a computer system, including measurement of acetabular shape, bone mass, acetabular abduction angle and anteversion angle, leg length discrepancy and offset. During the surgery, all data may be templated based on actual measurement data and displayed on the computer timely to determine the size and position of the prosthesis.

Step 702: determining spatial positions of a pelvis and a femur by using an optical locator, pelvic reference rack and femoral reference rack; registering the 3D model of the hip joint based on spatial position relationships between the surgical probe and both the pelvic reference rack and femoral reference rack to obtain a physical model of the hip joint, and matching the physical model of the hip joint with a preoperative planed model.

In this step, the pelvic reference rack and the femoral reference rack may be manually placed on the acetabular side and the femoral side, and a tracing element on the pelvic reference rack and femoral reference rack may be tracked by using a navigation camera of the system to determine spatial positions of the pelvis and femur of the patient. Correspondingly, the navigation camera tracks a tracing element at the tail of the surgical probe during the sampling of surgical probe points. Spatial positions of the sampled points are calculated through an algorithm, and thus spatial positions of the surgical probe, the pelvic reference frame and the femoral reference frame are integrated into a common coordinate system to register the 3D model of the hip joint. Corresponding sampled points will be displayed in the 3D model of the hip joint, and precise registration of surfaces of femoral side and acetabular side will be performed through a point cloud registration algorithm. After registration is completed between the femoral side and the acetabular side, the acetabular side is rasped and the femur is reamed. A predetermined type of acetabular shell and femoral stem are implanted into the femoral side and the acetabular side respectively after rasping the acetabular side and reaming the femur.

Step 703: placing an acetabular prosthesis in the hip joint by using a handheld control module instrument based on a registration result between a preoperative plan and the physical model of the hip joint, monitoring the position of the prosthesis in real-time during surgery, and manually adjusting a rotation center, anteversion angle, abduction angle, and insertion depth of the acetabular prosthesis by using a handheld control device to accurately perform the preoperative plan during the surgery.

In the navigation method for joint replacement surgery provided by embodiments of the present application, a 3D model of the hip joint is obtained before the surgery based on the medical image data of the hip joint, and then a preoperative plan is performed to stimulate a placement position, size and angle of a prosthesis and other information based on the 3D model of the hip joint. During the surgery, spatial positions of a femur and a pelvis are tracked by using a pelvic reference rack and a femoral reference rack, and the 3D model of the hip joint is registered based on spatial position relationships between a surgical probe and both the pelvic reference rack and the femoral reference rack. The structure of the hip joint of a patient may be accurately reflected through the 3D model of the hip joint, which allows a surgeon to have a very clear construe of the placement position of the prosthesis, and avoids complex processes of preoperative positioning and matching plan required by previous navigation systems. In embodiments of the present application, the preoperative plan is performed based on the 3D model, and intraoperative navigation is performed by using spatial positioning methods, which provides a doctor with visual surgical surgery monitoring information, assists the doctor in completing precise surgical operations, avoids dangerous areas to the maximum extent, and improves safety of the surgery.

The navigation method for joint replacement surgery described in this embodiment may be configured to execute the above method embodiments, and the principle and effect are similar, which will not be repeated here.

Figure 7:
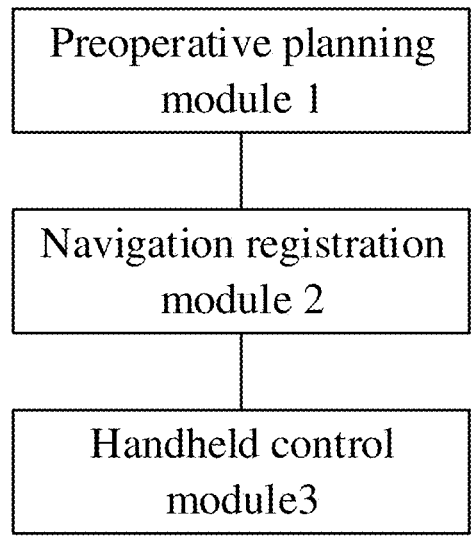
FIG. 7 is a structural schematic diagram of a handheld navigation robot according to an embodiment of the present application.

Another embodiment of the present application provides a handheld navigation robot based on the same invention concept. As shown in FIG. 7, an embodiment of the present application provides a handheld navigation robot, including a preoperative planning module 1, a navigation registration module 2, and a handheld robot processing module 3.

The preoperative planning module 1 is configured to segment and reconstruct a hip joint based on obtained medical image data of the hip joint to obtain a three-dimensional (3D) model of the hip joint, and perform a preoperative planning to determine a placement position, size and angle of a prosthesis based on the 3D model of the hip joint.

The navigation registration module 2 is configured to determine a spatial position of the pelvis by using a pelvic reference rack, and register the 3D model of the hip joint based on spatial position relationships between a surgical probe and both the pelvic reference rack and the femoral reference rack, to obtain a physical model of the hip joint.

The handheld robot processing module 3 is configured to rasp an acetabulum by using the handheld control device based on the physical model of the hip joint.

In this embodiment, preoperative scanning of the pelvis and both lower extremities of a patient may be performed by an imaging device (CT/MRI/X-ray) to generate a preoperative 3D view of the pelvis and both lower extremities. The navigation system for joint replacement surgery reads a CT image in DICOM format before the surgery, and segments the hip joint images to obtain a plurality of segmented images. A personalized complex hip joint 3D model including a virtual pelvis and a virtual femur may be reconstructed based on the image data corresponding to a plurality of segmented images to enable a surgeon to fully evaluate the condition of the patient before the surgery by using the hip joint 3D model and use a system software to plan a surgical approach and simulate a hip joint (the femoral side and acetabular side) surgical plan. The surgical plan includes surgical information such as the position, the size, and the angle of the implant of the prosthesis. Embodiments of the present application may achieve medical image processing on a regular computer, and allow a doctor to dissect visualized 3D images at will. In the navigation system for joint replacement surgery, lesion information is visually clear and easy for surgery operations.

In this embodiment, the navigation system for joint replacement surgery is imported through a computer system, including measurement of acetabular shape, bone mass, acetabular abduction angle and anteversion angle, leg length discrepancy and offset. During the surgery, all data may be templated based on actual measurement data and displayed on the computer timely to determine the size and position of the prosthesis.

In this embodiment, the pelvic reference rack and the femoral reference rack may be manually placed on the acetabular side and the femoral side, and a tracing element on the pelvic reference rack and femoral reference rack may be tracked by using a navigation camera of the system to determine spatial positions of the pelvis and femur of the patient. Correspondingly, the navigation camera tracks a tracing element at the tail of the surgical probe during the sampling of surgical probe points. Spatial positions of the sampled points are calculated through an algorithm, and thus spatial positions of the surgical probe, the pelvic reference frame and the femoral reference frame are integrated into a common coordinate system to register the 3D model of the hip joint, thus establishing the corresponding relationship between the virtual image and the patient entity, realizing matching verification and guidance between actual surgery and virtual surgery. Corresponding sampled points will be displayed in the 3D model of the hip joint, and precise registration of surfaces of femoral side and acetabular side will be performed through a point cloud registration algorithm. After registration is completed between the femoral side and the acetabular side, the acetabular side is rasped and the femur is reamed. A predetermined type of acetabular shell and femoral stem are implanted into the femoral side and the acetabular side respectively after rasping the acetabular side and reaming the femur. The navigation camera dynamically tracks a current position of the surgical instrument relative to an anatomical structure of the patient through infrared imaging.

In this embodiment, the handheld robot is used to rasp the acetabulum after completing the acetabular side registration in the physical model of the hip joint.

In this embodiment, hip replacement surgery requires high surgical requirements, but traditional instrument assistance easily leads to uncertainty of the placement of the prosthesis, which takes a considerable amount of time to implant the prosthesis into a correct position. In this embodiment, advanced imaging devices (CT/MRI/X-ray) are integrated, 3D models of the pelvis and both lower extremities are obtained based on an imaging examination result, and computer-aided medical imaging technology is used for 3D image reconstruction and fusion. The condition of the patient is fully evaluated before the surgery, a surgical path is planned to simulate a surgical plan, and a surgical approach and surgical information such as the size, position, and angle of prosthesis placement are determined. By tracking the surgical instrument through the spatial positioning method, the accuracy and feasibility of the surgery are significantly improved and navigation supports are provided for surgeons, which makes the surgery more accurate, safe, and efficient.

In an embodiment, the preoperative planning module includes three parts: a human-machine interaction interface, a motor control, and an image signal obtaining, which are all programmed in C++ and may run in the Windows operating system. Intraoperative surgical images and plan surgical paths can be transmitted, intraoperative navigation is performed by controlling the data network interface of this module. The system adopts an integrated design concept, which makes the system structure compact and occupies less surgical space. This modular design allows the system to be easily disassembled and assembled, which not only improves the clinical adaptability of the system but also facilitates disinfection. Moreover, the system has no special requirements for the surgical environment and surgical instruments.

In an embodiment, fast interface technology (data interface and mechanical interface) is used between functional modules to facilitate the assembly of the framework and the connection of drive motors and cables.

In this embodiment, a new type of navigation control technology is adopted. A handheld navigator based on optical recognition is adopted. A conversion mode is developed, which may achieve fast and slow control, 360° orientation fixation and positive and negative rotation, and guide the control system to read and analyze the original data, obtain its own coordinate system, and establish a mapping relationship with the handheld robot, to determine the quantitative relationship between its output data through calibration. First, a rotation control model of 360° is established to achieve the conversion of multiple control modes, the optimal effect during human-machine interaction is then determined, and the control mode that meets the intention of the operator is selected. Second, software interaction will optimize the display of its state to reduce the impact of physiological shaking on the operator during the control process. Finally, the high feasibility and universality in human-computer interaction applications of this mode have been effectively verified based on experiments. The traditional manual surgical mode not only requires proficient skills and rich clinical experience, but also has a long surgical time and a large workload, inevitably leading to personnel fatigue, which may affect surgical effect, or even causes medical accidents.

In an embodiment, specialized supporting instruments include: a handheld navigator, a navigation press-fitting rod, a pelvic reference rack (a pelvic reference rack adapter), a probe calibration rack, a surgical probe, a femur reference rack, a quick-connection positioning needle and supporting auxiliary tools. The position of the surgical probe in the patient coordinate system and the position relationship of the surgical probe in the model marked point coordinate system are used to transform the actual sampled surgical probe position into the coordinate system where the preoperative reconstructed 3D lesion model is located through coordinate transformation based on a 3D model during the surgery. The system is simple and stable, and may also meet accuracy requirements of surgical navigation, enable the instrument to move and locate in space within the body of the patient, enhance the ability to adjust the end posture of the surgical instrument, has good flexibility, and also meets the requirement of completing surgical operations in narrow spaces. The handheld navigator is configured to a power system that combines a power system and a light sensing system to drive the acetabular ream handle to complete intraoperative navigation. The handheld surgical robot navigation system is a connection structure that combines the power system with the light sensing system. The connection structure includes: a navigation ring having an end rotationally connected to the power system, which avoids the problem of limited orientation for having an autorotation joint. The navigation press-fitting rod is configured to perform the press-fitting operation during the operation process of the hip joint surgery. The pelvic reference rack is configured to track the position of the pelvic, and is used in conjunction with a 3-pin pelvic forceps and the pelvic reference rack adapter. The probe calibration rack is configured to perform preoperative calibration of the probe and perform accuracy verification on the surgical probe. The surgical probe, configured to sample several points on the anatomical structure of the patient. The femoral reference rack is configured to track the position of the femur. The quick-connection needles are configured for fixing during the surgery, and have the length of 3 mm and 4 mm respectively.

Figure 13:
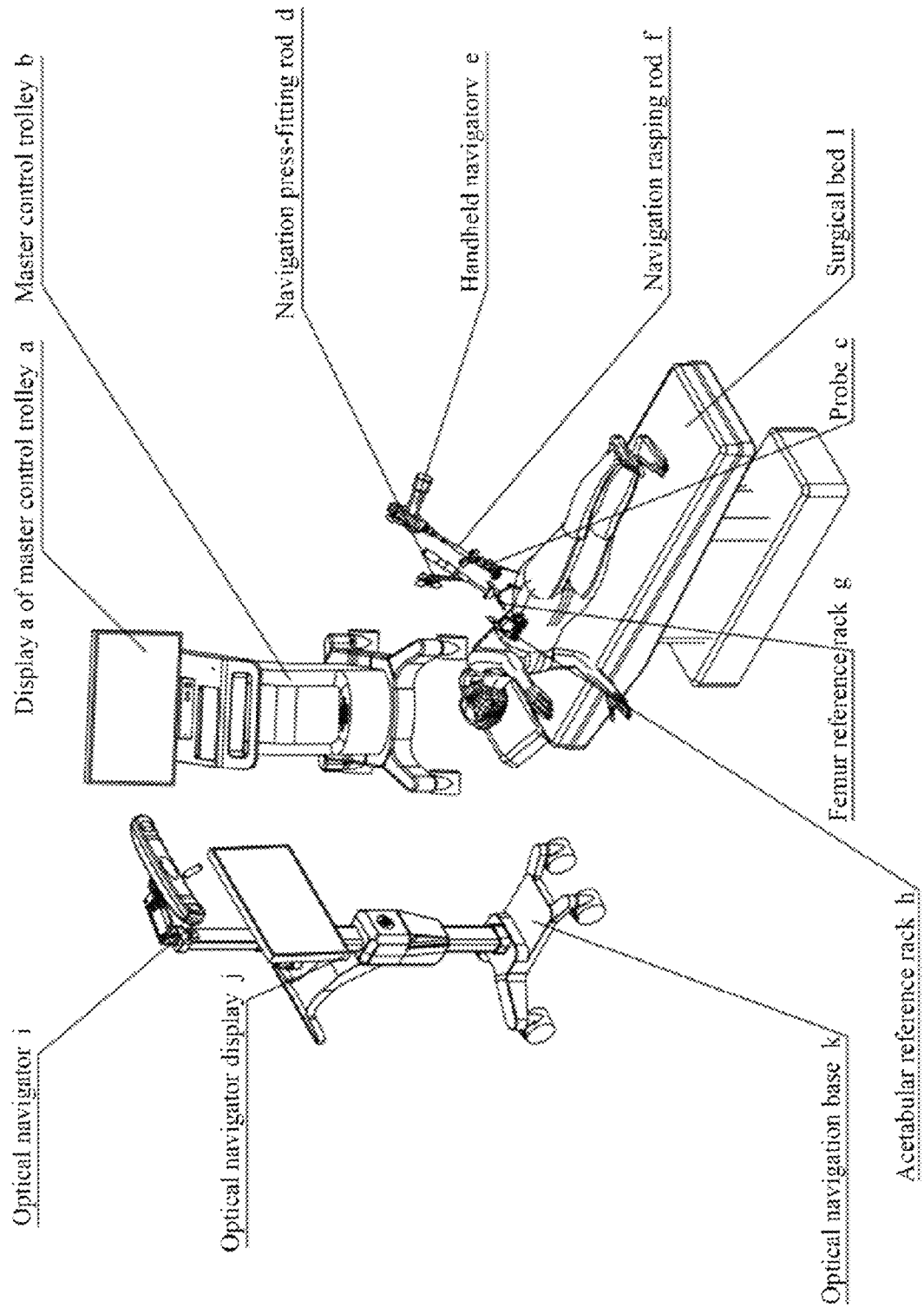
FIG. 13 is a schematic diagram of an application scenario of a navigation system for joint replacement surgery and a handheld navigation robot according to an embodiment of the present application.
Figure 14:
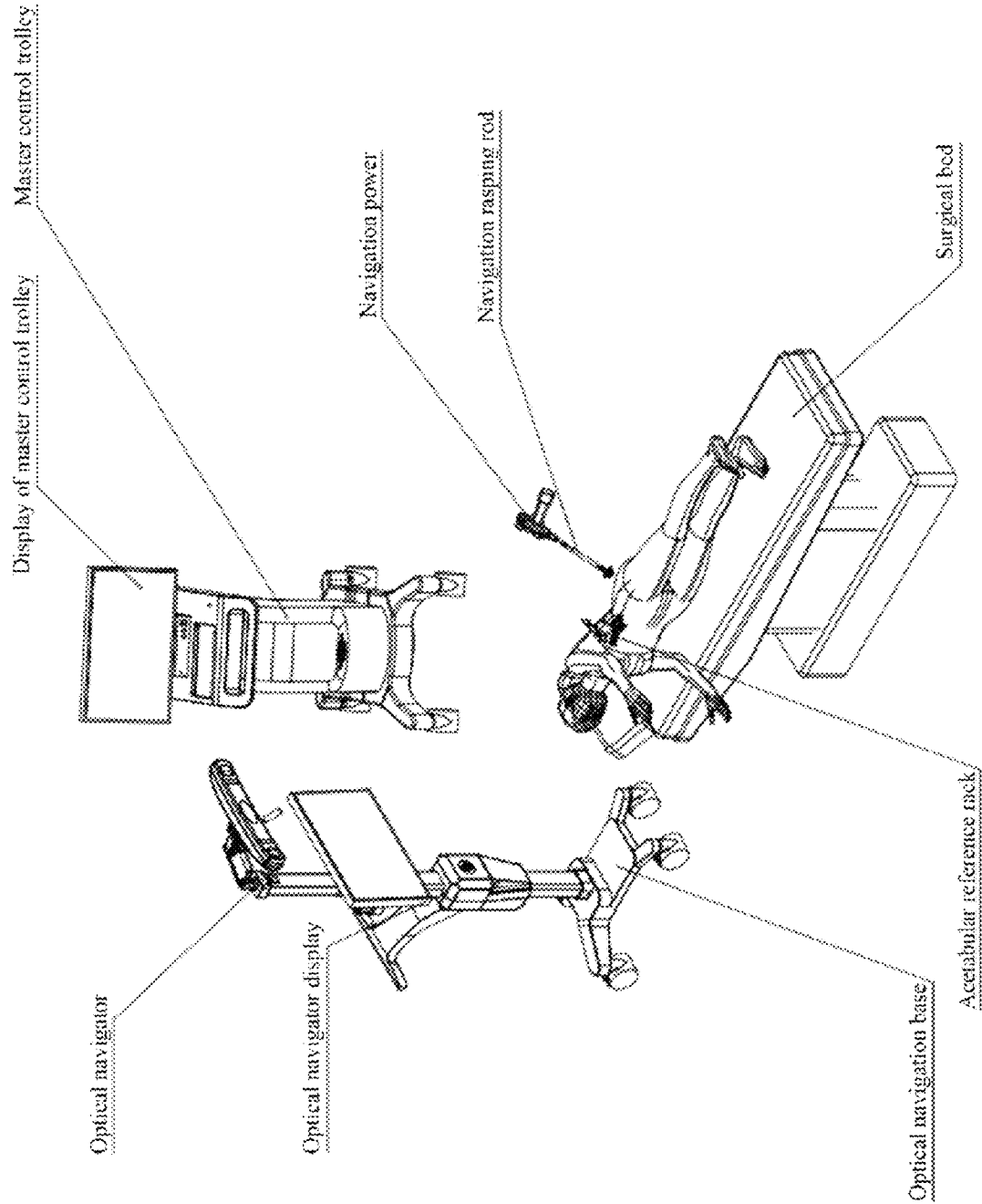
FIG. 14 is a schematic diagram of a rasping scenario of a navigation system for joint replacement surgery and a handheld navigation robot according to an embodiment of the present application.
Figure 15:
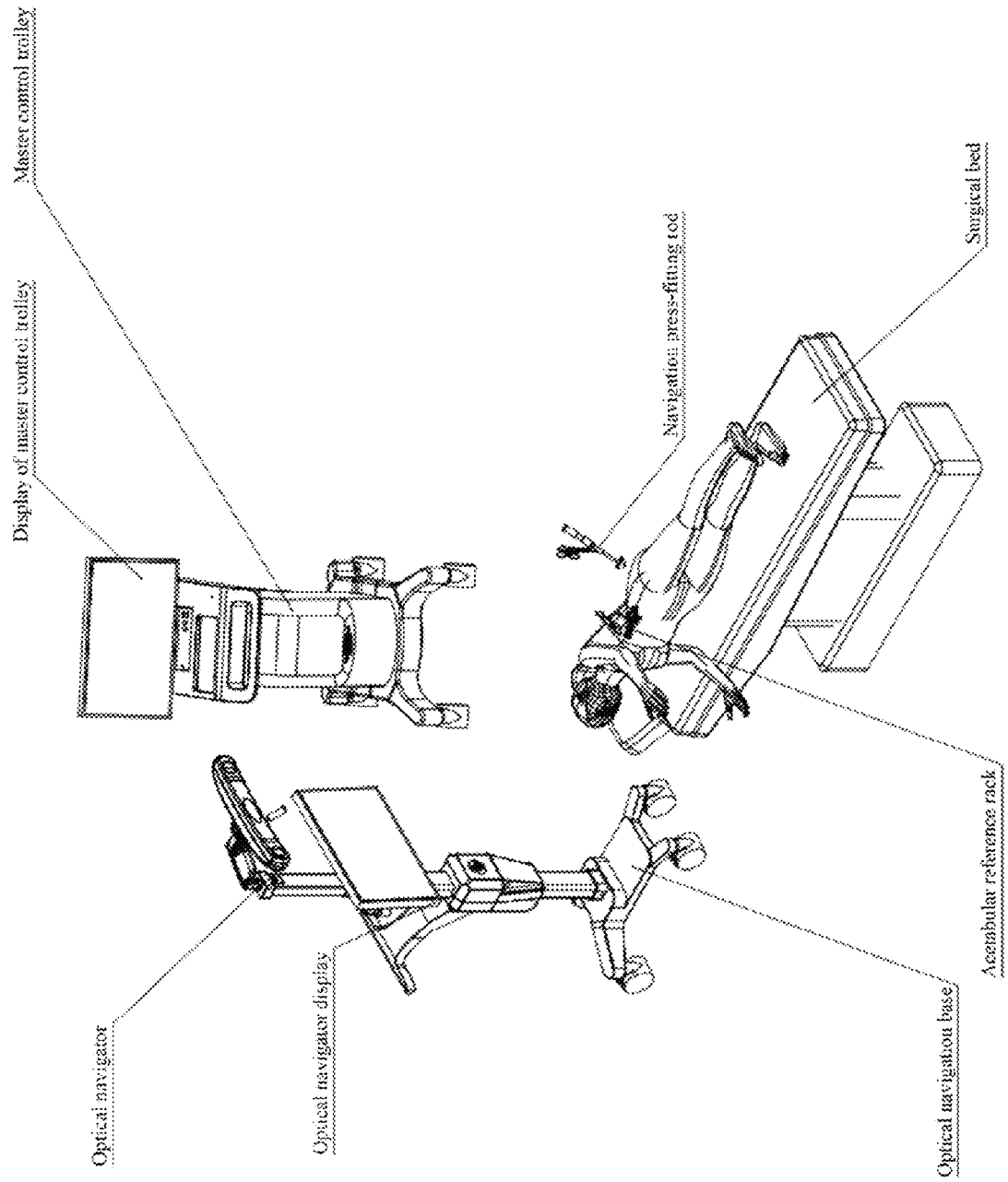
FIG. 15 is a schematic diagram of a press-fitting scenario of a navigation system for joint replacement surgery and a handheld navigation robot according to an embodiment of the present application.

As shown in FIG. 13, the application scenario diagram of a navigation system for joint replacement surgery and a handheld navigation robot is provided by an embodiment of the present application, where α represents a main control trolley display, which is used to complete preoperative planning and display real-time information of the entire surgical process; b represents the main control trolley, configured to carry the main control trolley display a and may move freely; i represents an optical navigator, configured to track the spatial positions of a handheld navigator e, a probe c, a femur reference rack g, a pelvic reference rack h and a navigation press-fitting rod d; c represents a surgical probe, configured to collect some points on the anatomical structure of the patient; d represents a navigation press-fitting rod, configured to perform the press-fitting operation in a hip joint surgery; e represents a handheld navigator, f represents a rasping rod, connected to the handheld navigator e, and configured to rasp the acetabular side during the surgery; g represents a femur reference rack, configured to locate the position of the femur of the patient; h represents an acetabular reference rack, configured to locate the position of the acetabular side of the patient, and used in conjunction with a 3-pin pelvic forceps and the pelvic reference rack adapter; j represents the optical navigator display, configured to display the spatial postures of the handheld navigator e, the probe c, the femur reference rack g, the acetabular reference rack h, and the navigation press-fitting rod d captured by the optical navigator i; k represents an optical navigation base, configured to carry the optical navigator i and the optical navigator display j and may move freely; l represents a surgical bed. As shown in FIG. 14 and FIG. 15, the present embodiment first performs the rasping operation on the acetabular side, and then performs the press-fitting operation on the acetabular side.

In the handheld navigation robot provided by the embodiments of the present application, a 3D model of the hip joint is obtained before the surgery based on the medical image data of the hip joint, and then a preoperative plan is performed to stimulate a placement position, size and angle of a prosthesis and other information based on the 3D model of the hip joint. During the surgery, the spatial position of a pelvis is tracked by using a pelvic reference rack, the 3D model of the hip joint is registered based on the spatial position relationship between the surgical probe and the pelvic reference rack, and the acetabulum is rasped based on the registered the physical model of the hip joint by using the handheld robot. In embodiments of the present application, the preoperative plan is performed based on the 3D model, intraoperative navigation is performed by using spatial positioning methods, and an intelligent rasping operation is performed on the acetabulum through the handheld robot, which provides a doctor with visual surgical surgery monitoring information, assists the doctor in completing precise surgical operations, avoids dangerous areas to the maximum extent, achieve fast, slow and 3600° rotation control of the rasping operation, thereby not only improving safety of the surgery, but also determining the optimal effect in the human-machine interaction process, to select the control mode that conforms to the intention of the operator.

Figure 8:
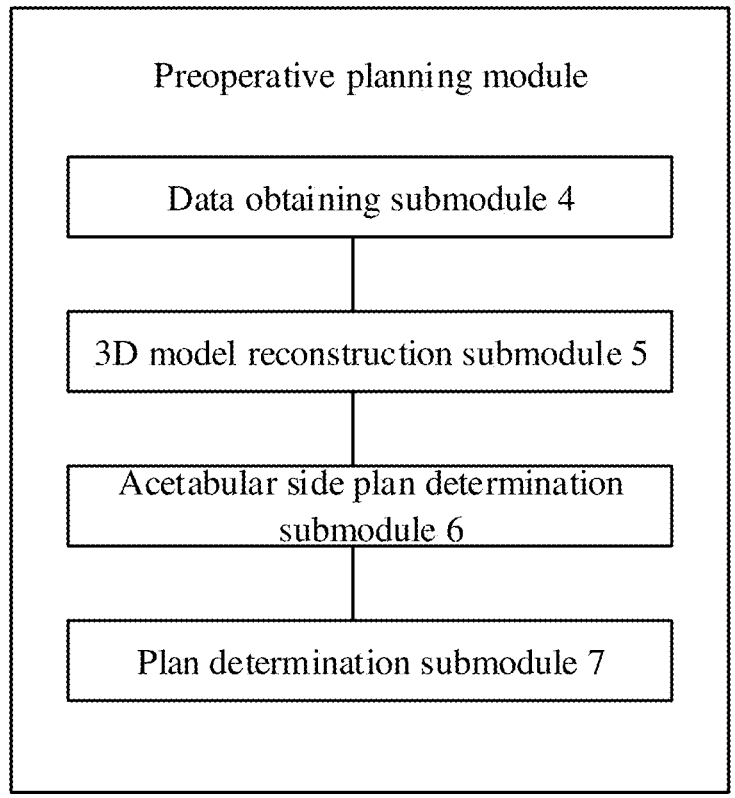
FIG. 8 is a schematic diagram of a preoperative planning module of a handheld navigation robot according to an embodiment of the present application.

Based on the above-mentioned embodiments, referring to FIG. 8, the schematic diagram of a preoperative planning module of a handheld navigation robot is provided by an embodiment of the present application. As shown in FIG. 8, the preoperative planning module 1 includes: a data obtaining submodule 4, a 3D model reconstruction submodule 5, an acetabular side plan determination submodule 6, and a plan determination submodule 7.

The data obtaining submodule 4 is configured to obtain the medical image data of the hip joint.

The 3D model reconstruction submodule 5 is configured to segment and reconstruct the hip joint based on the obtained medical image data of the hip joint to obtain a 3D model of the hip joint.

The acetabular side plan determination submodule 6 is configured to determine the acetabular side prosthesis implantation plan based on the 3D model of the hip joint.

The plan determination submodule 7 is configured to determine whether an acetabular side prosthesis implantation plan determined by the acetabular side plan determination submodule is suitable: in case that the acetabular side prosthesis implantation plan determined by the acetabular side plan determination submodule is unsuitable, trigger the acetabular side plan determination submodule to re-determine the acetabular side prosthesis implantation plan; in case that the acetabular side prosthesis implantation plan determined by the acetabular side plan determination submodule is suitable, determine the acetabular side prosthesis implantation plan determined by the acetabular side plan determination submodule as the preoperative plan scheme.

In an embodiment, the handheld robot navigation system for joint replacement surgery segments the hip joint image into a plurality of segmented images after reading DICOM format CT images before the surgery, to obtain image data corresponding to the plurality of segmented images.

In an embodiment, a personalized complex hip joint 3D model including the virtual pelvis and femur is reconstructed based on the image data obtained from the data obtaining submodule.

In an embodiment, the surgeon may develop a plan for rasping acetabular and implanting acetabular shell based on the structure of the acetabular side in the 3D model of the hip joint, including information such as surgical approached, rasping frequency, size, position, and angle of the acetabular shell.

In an embodiment, after developing the acetabular side plan, the surgeon need to perform evaluation and analysis, and re-develop the surgical plan that do not meet the standard to ensure that the surgical plan generated by preoperative plan is the best plan. The embodiments of the present application may provide convenience for the doctor to perform surgical operations from visual, tactile, and auditory perspectives, expand operational skills of the doctor, effectively improve the quality of surgical diagnosis and evaluation, precision operations, and surgical training, and shorten the rehabilitation cycle of the patient.

Figure 9:
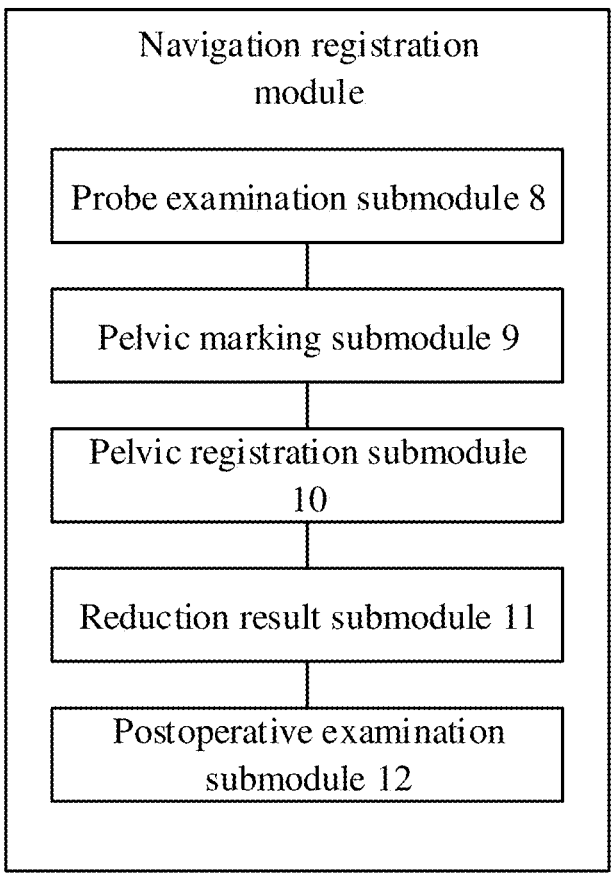
FIG. 9 is a schematic diagram of a navigation registration module of a handheld navigation robot according to an embodiment of the present application.

Based on the above-mentioned embodiments, referring to FIG. 9, a schematic diagram of a navigation registration module for a handheld navigation robot is provided by an embodiment of the present application. As shown in FIG. 9, the navigation registration module 2 includes: a probe examination submodule 8, a pelvic marking submodule 9, and a pelvic registration submodule 10.

The probe examination submodule 8 is configured to perform accuracy verification on the surgical probe by using a probe calibration rack;

The pelvic marking submodule 9 is configured to sample spatial positions of three or more points on an acetabular side structure by using the surgical probe;

The pelvic registration submodule 10 is configured to register the acetabular side in the 3D model of the hip joint based on spatial position relationships between three or more points on the acetabular side structure sampled by using the surgical probe and the pelvic reference rack.

In an embodiment, accuracy verification for the surgical probe is required before intraoperative sampling. The tip of the surgical probe will be tapped to each examining point on the calibration rack of the probe in turn. After tapping all examining points, the sampling accuracy of the surgical probe will be displayed on the system. The surgical probe that does not meet the preset standards will be adjusted to meet the surgical operation requirements.

In an embodiment, the tip of the surgical probe is used to tapped three or more different positions on the acetabular side during the surgery, and the acetabular side in the 3D model of the hip joint is registered based on spatial position relationships between three or more points on the acetabular side structure sampled by using the surgical probe and the pelvic reference rack. It may be understood that the navigation registration module 2 needs to perform a coordinate system registration between the intraoperative position of the patient and preoperative scanning data (such as CT and MRI) to find a conversion relationship between the preoperative scanning data and the intraoperative position of the patient, and modify the 3D model of the hip joint generated by the preoperative plan based on the intraoperative position of the patient to reduce the error in spatial positions of marked points during the preoperative plan process, thereby improving the registration accuracy greatly.

In an embodiment of the present application, a point cloud selected in the scanning data before the surgery is fitted with a point cloud calibrated by the doctor to find the most suitable rotation matrix. When calibrating a point on the body of the patient, the doctor will refer to the point selected before the surgery. In case that the point calibrated by the doctor and the point selected before the surgery are not in the same position on the body, the position of the selected point cloud before the surgery needs to be corrected in real-time based on the spatial position relationship and structure of the point cloud calibrated by the doctor, so as to make a final registration result have relatively high accuracy. The point cloud registration algorithm is as follows.

Using the surgical probe to sample points on three or more patient anatomical structures is taken as an example. The minimum unit of this registration algorithm is a triangle. Assuming that the points marked by the doctor during the surgery are A, B and C, and the corresponding preoperative plan points are a, b, and c, and it may be defaulted that the points marked by the doctor are all on the surface of human tissue. Therefore, points a', b' and c' need to be found in the neighborhood of a, b and c, to make the triangle ABC and triangle a'b'c' congruent, where points a'b'c' are all on the surface of human tissue, resulting in a high degree of overlap between the positions of points a'b'c' and points ABC on the human tissue, as the triangle has uniqueness. As shown in FIG. 12, a schematic diagram of the registration process of a navigation system for joint replacement surgery is provided by an embodiment of the present application. On the left side of this figure, A, B and C are the points marked by the doctor during the surgery, and a, b and c on the right side are the points planned before the surgery. It may be seen that (A, B, C) and (a, b, c) have a significant spatial position error, and blank marked points on the right side are point sets in the neighborhood space of a, b and c. a', b' and c' are selected from a large number of blank marked points. The triangle consisted of a', b' and c' and the triangle consisted of A, B and C are basically congruent triangles. At this time, Spatial positions of a, b, and c planned before the surgery are adjusted to spatial positions of a', b' and c', and an ICP registration mode is used to register the points marked during the surgery with the points planned before the surgery, so as to achieve accurate registration of the surfaces of the femoral side and the acetabular side.

In an embodiment, a personalized pelvic model is established through optical tracking software and the position of the acetabular prosthesis is simulated by the tracking system. During the entire implantation process, the data of the angle of acetabular prosthesis are always displayed on a computer screen, and the position of the acetabular prosthesis is updated and displayed in real-time in the form of simulation, which makes the surgeon have a clear understanding about the position of the prosthesis, avoids the tedious process of preoperative positioning and matching plan required by a traditional navigation system. The system software may accurately detect and calculate the 3D data of an object, and determine specific orientations and angles of the object.

Figure 10:
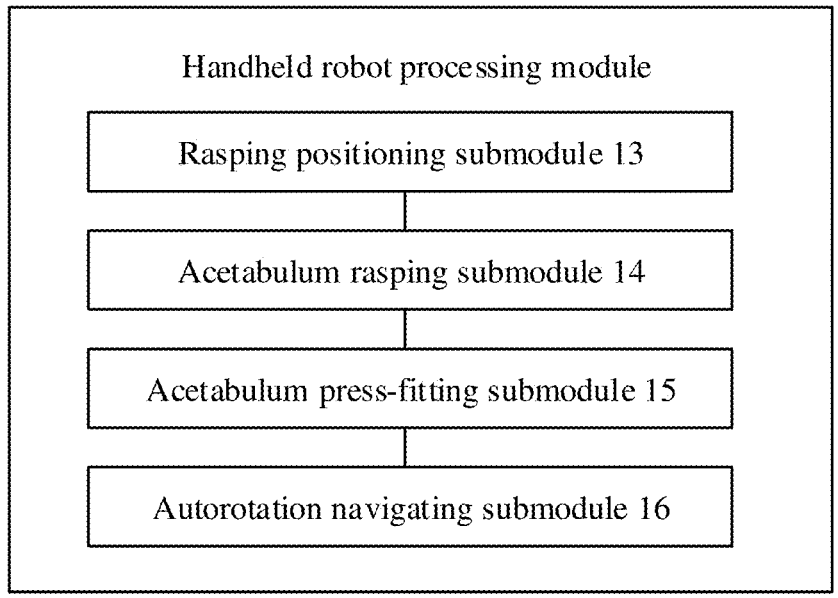
FIG. 10 is a schematic diagram of a handheld robot processing module of a handheld navigation robot according to an embodiment of the present application.

Based on the above-mentioned embodiments, referring to FIG. 10, a schematic diagram of a handheld robot processing module for a handheld navigation robot is provided by an embodiment of the present application. As shown in FIG. 10, the handheld robot processing module 3 includes: a rasping positioning submodule 13, an acetabulum rasping submodule 14 and an acetabulum press-fitting submodule 15.

The rasping positioning submodule 13 is configured to obtain the spatial position of the handheld navigator in the acetabular side structure, and register the acetabular side in the 3D model of the hip joint based on the spatial position relationship between the handheld navigator in the acetabular side structure and the pelvic reference rack.

The acetabulum rasping submodule 14 is configured to perform a rasping operation on the acetabulum by using the rasping handle of the handheld navigator based on the registration results of the acetabular side in the 3D model of the hip joint.

The acetabulum press-fitting submodule 15 is configured to control the surgical instrument holding the acetabular shell to place the acetabular shell in the acetabulum and perform the press-fitting operation based on the physical model of the hip joint after rasping the acetabulum.

In an embodiment, the navigation camera of the system is used to track the spatial position of the handheld navigator in the acetabular side structure, and then the spatial position of the handheld navigator in the acetabular side structure and the spatial position of the pelvic reference rack are integrated into a common coordinate system to register the acetabular side in the 3D model of the hip joint.

In an embodiment, after successful registration of the acetabular side in the 3D model of the hip joint, the surgeon may use the handheld navigator to perform a rasping operation on the acetabulum. During the operation, the rotation joint on the handheld navigator may be used to adjust in 360° of different directions, so as to adapt to optical tracking and recognition in different directions.

In an embodiment, after rasping the acetabular side, the acetabular shell is placed in the acetabulum by controlling the surgical instrument holding the acetabular shell is controlled, and the press-fitting operation is performed by using the navigation pressing rod.

In an embodiment, the handheld navigator may assist the human arm in performing the rasping operation, and the handheld robot navigation system performs real-time navigation through technologies such as computer vision and robot positioning. During the surgery, the 3D vision system and motion calibration system are used to control the operation, and the infrared camera of the system dynamically tracks the current position of the surgical instrument relative to the anatomical structure of the patient. Embodiments of the present application combine traditional surgical tools with photosensitive balls to establish a handheld robot navigation system platform based on the optical navigation and force feedback. Optical tracking and positioning technologies are used to perform precise intraoperative positioning. The handheld navigator is combined with surgical instruments to perform actions and surgical operations of a doctor. The doctor is provided with visual surgical surgery monitoring information and assisted in completing precise surgical operations, dangerous areas are avoided to the maximum extent, the number of rasping and complications of the patient is greatly reduced, and safety of the surgery is improved.

In an embodiment, a personalized pelvic model is established through optical tracking software and the position of the acetabular prosthesis is simulated by the tracking system. During the entire implantation process, the data of the angle of acetabular prosthesis are always displayed on a computer screen, and the position of the acetabular prosthesis is updated and displayed in real-time in the form of simulation, which makes the surgeon have a clear understanding about the position of the prosthesis, avoids the tedious process of preoperative positioning and matching plan required by a traditional navigation system. The system software may accurately detect and calculate the 3D data of an object, and determine specific orientations and angles of the object.

In an embodiment, the handheld navigator helps to reduce the labor risk of medical workers, effectively avoiding the risk of the doctor working under radiation conditions and the probability of infection during the surgery. The emergence of the handheld navigator has promoted the progress of related technologies. It will not solely rely on the experience of doctors, and has become more standardized in disease detection and data acquisition, which greatly promotes the development of related medical technologies.

The embodiments of the present application use a handheld navigator to assist surgeon in rasping operations, having beneficial effects to reduce manufacturing costs and maintenance costs, make surgical robots more widely used, simplify the complex structural design of surgical robots, simplify operation steps, make it more convenient for the doctor. The handheld navigator is more miniaturized and operated in distance, and has a smaller equipment volume easy for transportation. Its remote surgery technology is more mature and intelligent, and has a certain degree of artificial intelligence, which is benefit to predict, evaluate and alert the related operations of the doctor.

Based on the above-mentioned embodiments, the handheld robot processing module 3 further includes an autorotation navigating submodule 16;

where the autorotation navigating submodule is connected to a rasping positioning submodule 13, and is configured to drive the rasping positioning submodule to achieve adjustment in different directions of 360° to adapt to optical tracking and recognition in different directions.

Figure 11:
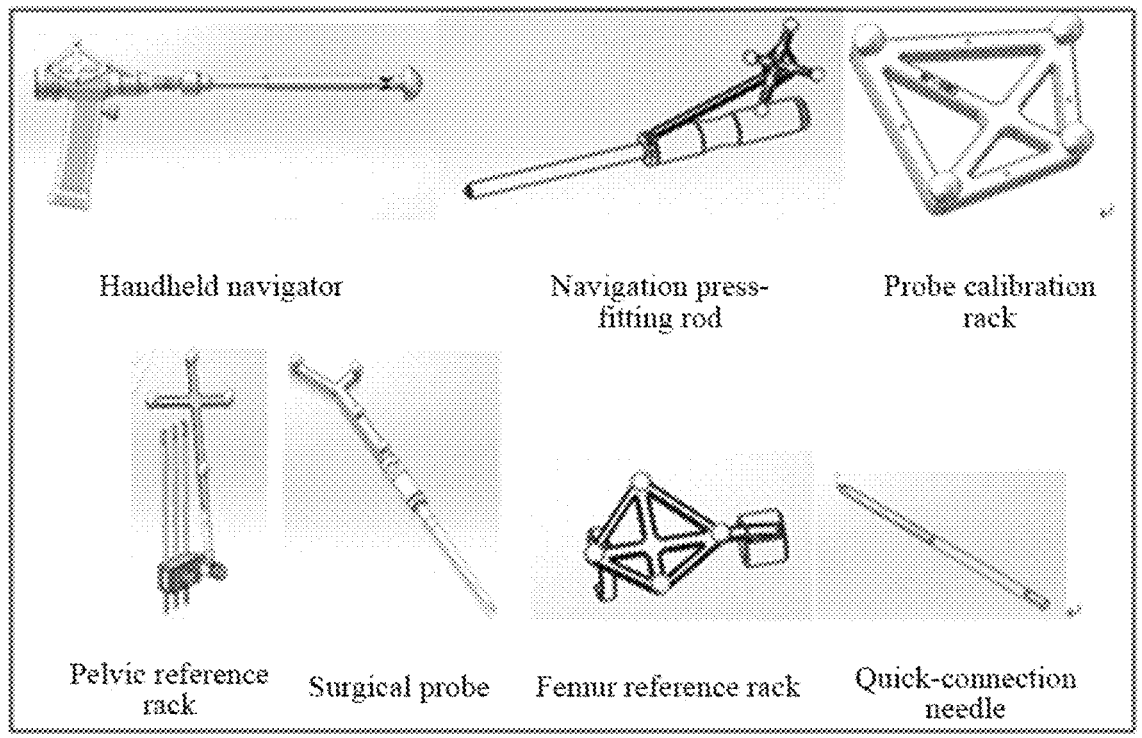
FIG. 11 is a schematic diagram of operating tools according to an embodiment of the present application.

In an embodiment, the handheld navigator includes an autorotation joint connected to the navigation ring, and may drive the navigation ring to achieve adjustment of 360° in different directions to adapt to optical tracking and recognition in different directions. Embodiments of the present application may achieve positioning conversion of 360° in different directions through the handheld navigator, thereby solving the problem of limited operating range and easily entering a crash state of existing navigation robots. FIG. 11 provides an example explanation of the operating tools required during the surgery.

Based on the above-mentioned embodiments, the navigation registration module 2 further includes: a reduction result submodule 11 and a postoperative examination submodule 12.

The reduction result submodule 11 is configured to sample spatial positions of three or more points on the acetabular shell by using a surgical probe, determine the placement position, size and angle of the acetabular shell in the acetabulum, and determine the surgical reduction result.

The postoperative examination submodule 12 is configured examine the motion range of the hip joint to evaluate a postoperative stability of the hip joint after the surgical reduction.

In an embodiment, it is determined whether to perform surgical reduction after the implantation of the acetabular shell based on the placement position, the size, and the angle of the acetabular shell in the acetabulum. The tip of the surgical probe is used to tap the spatial positions of three or more points on the acetabular shell after implanting the acetabular shell. The acetabular side of the 3D model of the hip joint is registered based on the spatial relationship between sampled points of the surgical probe and the pelvic reference rack to determine the placement position, size and angle of the acetabular shell in the acetabulum, and to determine whether to perform surgical reduction.

In an embodiment, after the surgical reduction, postoperative stability of the hip joint is evaluated by checking the motion range of the hip joint, the articular capsule is sutured, and the tissue layers are closed layer by layer.

In an embodiment, after completing the entire hip replacement surgery, the variation of the acetabular prosthesis abduction angle is reduced. The prosthesis is more compatible with the human body, the prosthesis installation process is more accurate, the surgical quality is significantly improved, and some postoperative complications may be effectively avoided.

Another embodiment of the present application further provides a navigation method for joint replacement surgery, including:

segmenting and reconstructing the hip joint based on obtained medical image data of the hip joint to obtain a three-dimensional (3D) model of the hip joint, and performing a preoperative planning to determine a placement position, size and angle of a prosthesis based on the 3D model of the hip joint;

determining spatial positions of a pelvis and a femur by using an optical locator, pelvic reference rack and femoral reference rack; registering the 3D model of the hip joint to obtain a hip joint model based on spatial position relationships between the surgical probe and both the pelvic reference rack and femoral reference rack to obtain a physical model of the hip joint, and matching the physical model of the hip joint with a preoperative planed model; and placing an acetabular prosthesis in the hip joint by using a handheld control module instrument based on a registration result between a preoperative plan and the physical model of the hip joint, monitoring the position of the prosthesis in real-time during surgery, and manually adjusting a rotation center, anteversion angle, abduction angle, and insertion depth of the acetabular prosthesis by using a handheld control device to accurately perform the preoperative plan during the surgery.

The method provided by the embodiment of the present application may be implemented by using the aforementioned navigation system for joint replacement surgery, and the principle and effect are similar, which will not be repeated here.

Figure 22:
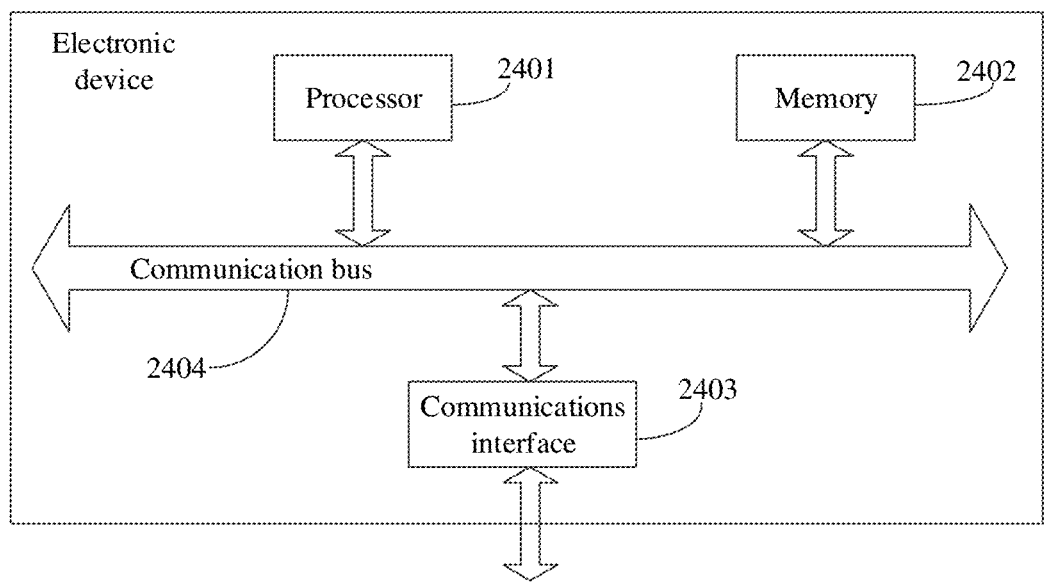
FIG. 22 is a schematic diagram of the structure of an electronic device according to an embodiment of the present application.

Based on the same invention idea, an embodiment of the present application provides an electronic device. FIG. 22 illustrates a schematic structural diagram of an electronic device, including: a processor 2201, a memory 2202, a communication interface 2203 and a communication bus 2204.

The processor 2201, memory 2202, communication interface 2203 communicate with each other through the communication bus 2204. The communication interface 2203 is used to achieve information transmission between various devices.

The processor 2201 is used to call the computer program in the memory 2202, and when executing the computer program, the processor implements all the steps of the navigation and positioning method for the joint replacement surgical robot described above. For example, the method includes: segmenting and reconstructing the hip joint based on obtained medical image data of the hip joint to obtain a three-dimensional (3D) model of the hip joint, and performing a preoperative planning to determine a placement position, size and angle of a prosthesis based on the 3D model of the hip joint; determining spatial positions of a pelvis and a femur by using the pelvic reference rack and the femoral reference rack; registering the 3D model of the hip joint to obtain a hip joint model based on spatial position relationships between the surgical probe and both the pelvic reference rack and the femoral reference rack to obtain a physical model of the hip joint, and controlling the surgical instruments holding the prosthesis to place the prosthesis in the hip joint based on the physical model of the hip joint.

Based on the same invention idea, an embodiment of the present application provides a non-transitory computer-readable storage medium having stored thereon computer programs, where the computer programs, when executed by a processor, cause the processor to perform all steps of the navigation and positioning method for the joint replacement surgical robot. For example, the method includes: segmenting and reconstructing the hip joint based on obtained medical image data of the hip joint to obtain a three-dimensional (3D) model of the hip joint, and performing a preoperative planning to determine a placement position, size and angle of a prosthesis based on the 3D model of the hip joint; determining spatial positions of a pelvis and a femur by using the pelvic reference rack and the femoral reference rack; registering the 3D model of the hip joint based on spatial position relationships between the surgical probe and both the pelvic reference rack and the femoral reference rack to obtain a physical model of the hip joint, and controlling the surgical instruments holding the prosthesis to place the prosthesis in the hip joint based on the physical model of the hip joint.

Further, the logic instructions in the above memory may be implemented in the form of a software functional unit and may be stored in a computer-readable storage medium when sold or used as a separate product. Based on this understanding, the solutions of the present application in essence, or the parts of the solutions of the present application that contribute to the related art or the parts of the solutions may be embodied in the form of a software product. The computer software product is stored in a storage medium, including a number of instructions to enable a computer device (may be a personal computer, server, or network device, etc.) to perform all or part of the steps of the method described in each embodiment of the present application. The aforementioned storage media include: USB flash disk, mobile hard disk, read-only memory (ROM), random access memory (RAM), disk or optical disk and other media that can store program code.

By describing the above embodiments, those skilled in the art may clearly understand that each embodiment may be implemented by software plus the necessary general hardware platform, of course, or only by hardware. Based on this understanding, the solutions of the present application in essence, or the parts of the solutions of the present application that contribute to the related art or the parts of the solutions may be embodied in the form of a software product. The computer software product is stored in a storage medium, such as ROM/RAM, disk or optical disk and other media, which store a number of instructions to enable a computer device (may be a personal computer, server, or network device, etc.) to perform the navigation and positioning method for the joint replacement surgical robot described in each embodiment or part of the embodiment of the present application.

Finally, it should be noted that the above embodiments are only used to illustrate the solutions of the present application, and are not limited thereto. Although the present application is described in detail with reference to the foregoing embodiments, those of ordinary skill in the art should understand that they may still modify the solutions described in each of the foregoing embodiments, or equivalently replace some of the features. These modifications or replacements do not depart the essence of the corresponding solutions from the scope of the solutions of each embodiment of the present application.

What is claimed is:

1. A navigation system for joint replacement surgery, comprising:
a preoperative planning module, configured to segment and reconstruct a hip joint based on obtained medical image data of the hip joint to obtain a three-dimensional model of the hip joint, and perform a preoperative planning to determine a placement position, a size and an angle of a prosthesis based on the 3D model of the hip joint for a preoperative plan;
a navigation registration module, configured to determine spatial positions of a pelvis and a femur by using an optical locator, a pelvic reference rack and a femoral reference rack, register the three-dimensional model of the hip joint based on spatial position relationships between a surgical probe and both the pelvic reference rack and the femoral reference rack to obtain a physical model of the hip joint, and match the physical model of the hip joint with a preoperative planned model;
a handheld control module, configured to place an acetabular prosthesis in the hip joint by using a handheld control module instrument based on a registration result between the preoperative planned model and the physical model of the hip joint, monitor a position of the prosthesis in real-time during the surgery, and manually adjust a rotation center, an anteversion angle, an abduction angle, and an insertion depth of the acetabular prosthesis by using a handheld control device to accurately perform the preoperative plan during the surgery;
wherein the preoperative planning module comprises: a data obtaining submodule, a three-dimensional model reconstruction submodule, an acetabular side plan determination submodule, a femoral side plan determination submodule and a plan determination submodule,
wherein the data obtaining submodule is configured to obtain the medical image data of the hip joint;
the three-dimensional model reconstruction submodule is configured to segment and reconstruct the hip joint based on the obtained medical image data of the hip joint to obtain the three-dimensional model of the hip joint;
the acetabular side plan determination submodule is configured to determine the rotation center, a diameter, the anteversion angle and the abduction angle of the acetabular based on the three-dimensional model of the hip joint, and determine the size and position of an acetabular side implant prosthesis based on the rotation center, the diameter, the anteversion angle and the abduction angle of the acetabular and a coverage rate of an acetabular shell;
the femoral side plan determination submodule is configured to determine a rotation center of a femoral head, a shape and an anatomical axis of a femoral medullary cavity and a collodiaphyseal angle of the femur based on the three-dimensional model of the hip joint and determine a size and position of a femoral side implant prosthesis based on the rotation center of the femoral head, the shape and anatomical axis of the femoral medullary cavity, the collodiaphyseal angle of femur, a leg length discrepancy and a femoral combined offset; and
the plan determination submodule is configured to determine whether an acetabular side prosthesis implantation plan determined by the acetabular side plan determination submodule and a femoral side prosthesis implantation plan determined by the femoral side plan determination submodule are suitable;
if the acetabular side prosthesis implantation plan determined by the acetabular side plan determination submodule and the femoral side prosthesis implantation plan determined by the femoral side plan determination submodule are unsuitable, trigger the acetabular side plan determination submodule and the femoral side plan determination submodule to re-determine the acetabular side prosthesis implantation plan and the femoral side prosthesis implantation plan;
if the acetabular side prosthesis implantation plan determined by the acetabular side plan determination submodule and the femoral side prosthesis implantation plan determined by the femoral side plan determination submodule are suitable, determine the acetabular side prosthesis implantation plan determined by the acetabular side plan determination submodule and the femoral side prosthesis implantation plan determined by the femoral side plan determination submodule as the preoperative plan scheme.

2. The navigation system of claim 1, wherein the navigation registration module comprises: a probe examination submodule, a femur marking submodule, a femur registration submodule, a femur neck osteotomy submodule, a reaming and femoral stem placing submodule, a pelvis mark submodule and a pelvis registration submodule,
wherein the probe examination submodule is configured to perform accuracy verification on the surgical probe by using a probe calibration rack;
the femur marking submodule is configured to sample spatial positions of three or more points on a femoral anatomical structure by using the surgical probe;
the femur registration submodule is configured to register the femur in the three-dimensional model of the hip joint based on spatial position relationships between three or more points on the femoral anatomical structure sampled by using the surgical probe and the femoral reference rack;
the femur neck osteotomy submodule is configured to determine a position of the femur neck osteotomy based on a registration result of the femur in the three-dimensional model of the hip joint;
the reaming and femoral stem placing submodule is configured to ream the femur and place the femoral stem based on the position of the femur neck osteotomy;
the pelvic femur marking submodule is configured to sample spatial positions of three or more points on an acetabular side structure by using the surgical probe; and
the pelvic registration submodule is configured to register the acetabular side in the three-dimensional model of the hip joint based on spatial position relationships between three or more points on the acetabular side structure sampled by using the surgical probe and the pelvic reference rack.

3. The navigation system of claim 2, wherein the handheld control module comprises: an acetabulum rasping submodule, an acetabulum press-fitting submodule and a reduction result submodule,
- wherein the acetabulum rasping submodule is configured to rasp an acetabulum by using the handheld control device based on a registration result of the acetabular side in the three-dimensional model of the hip joint;
- the acetabulum press-fitting submodule is configured to control a surgical instrument holding an acetabular shell to place the acetabular shell in the acetabulum and complete a press-fitting operation by using the handheld control device based on the physical model of the hip joint after rasping the acetabulum, wherein the control of the surgical instrument holding the acetabular shell to place the acetabular shell in the acetabulum and complete the press-fitting operation by using the handheld control device refers to: manually adjust the rotation center, the anteversion angle, the abduction angle, and the insertion depth of the acetabular prosthesis by using the handheld control device to accurately perform the preoperative plan during the surgery; and
- the reduction result submodule is configured to determine a surgical reduction result based on an alignment between the femoral stem and the femoral anatomical structure, a placement position, a size, and an angle of the acetabular shell in the acetabulum.

4. The navigation system of claim 3, wherein the reduction result submodule is configured to:
- sample spatial positions of three or more points on the acetabular shell by using the surgical probe, determine the placement position, the size, and the angle of the acetabular shell in the acetabulum and measure the alignment between the femoral stem and the femoral anatomical structure to determine the surgical reduction result.

5. The navigation system of claim 3, wherein the handheld control module further comprises an autorotation navigating submodule,
- wherein the autorotation navigating submodule is connected to a rasping positioning submodule and is configured to drive the rasping positioning submodule to achieve adjustment in different directions of 360° to adapt to optical tracking and recognition in different directions.

6. The navigation system of claim 1, wherein the navigation registration module further comprises a postoperative examination submodule,
- wherein the postoperative examination submodule is configured to examine a motion range and limb length of the hip joint to evaluate a postoperative stability of the hip joint after surgical reduction.

* * * * *